US009526601B2

(12) United States Patent
Boden et al.

(10) Patent No.: US 9,526,601 B2
(45) Date of Patent: Dec. 27, 2016

(54) MEDICAL DEVICES AND IMPLANT ASSEMBLIES FOR IMPLANT CAPTURE

(71) Applicant: Boston Scientific Scimed, Inc., Maple Grove, MN (US)

(72) Inventors: Mark W. Boden, Harrisville, RI (US); Isaac Ostrovsky, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 183 days.

(21) Appl. No.: 14/195,606

(22) Filed: Mar. 3, 2014

(65) Prior Publication Data

US 2014/0257023 A1    Sep. 11, 2014

Related U.S. Application Data

(60) Provisional application No. 61/773,972, filed on Mar. 7, 2013.

(51) Int. Cl.
| | | |
|---|---|---|
| *A61F 2/00* | (2006.01) | |
| *A61B 17/06* | (2006.01) | |
| *A61B 17/04* | (2006.01) | |
| *A61B 17/00* | (2006.01) | |

(52) U.S. Cl.
CPC ............. *A61F 2/0045* (2013.01); *A61B 17/04* (2013.01); *A61B 17/06109* (2013.01);
(Continued)

(58) Field of Classification Search
CPC .................. A61F 2/0045; A61B 2017/00805; A61B 17/06109; A61B 17/04; A61B 2017/06042; A61B 2017/06071; A61B 17/06166
See application file for complete search history.

(56) References Cited

U.S. PATENT DOCUMENTS

| | | | | |
|---|---|---|---|---|
| 3,946,740 A | * | 3/1976 | Bassett | A61B 17/0469 606/145 |
| 5,730,747 A | * | 3/1998 | Ek | A61B 17/0469 606/139 |

(Continued)

FOREIGN PATENT DOCUMENTS

| | | |
|---|---|---|
| WO | 96/39948 A1 | 12/1996 |
| WO | 2009/075800 A1 | 6/2009 |

(Continued)

OTHER PUBLICATIONS

Invitation to Pay Additional Fees and Partial Search Report for PCT Patent Application No. PCT/US2014/020387 mailed on Jun. 27, 2014, 5 pages.

(Continued)

*Primary Examiner* — Christine H Matthews
*Assistant Examiner* — Joshua D Lannu
(74) *Attorney, Agent, or Firm* — Brake Hughes Bellermann LLP

(57) ABSTRACT

This invention generally relates to devices and methods that allow an operator to position an implant into the body of a patient without the need for direct-vision of the operator or the need to hand-guide a needle in order to capture an implant. In one aspect, a multi-arm delivery device includes a receiving arm that releasably holds an implant in place for capture and a clamping arm that includes a needle deployment mechanism for advancing a needle directly to the implant for capture and for retracting the needle with the implant attached to deliver the implant into the desired location. In one embodiment, the needle includes a plurality of retaining slots. In another embodiment, an end portion of the implant is configured to receive a needle into the end portion and at least some of the end portion of the implant is configured to be retained into one or more retaining slots of the needle.

16 Claims, 20 Drawing Sheets

(52) U.S. Cl.
CPC ............... *A61B 17/06166* (2013.01); *A61B 2017/00805* (2013.01); *A61B 2017/06042* (2013.01); *A61B 2017/06071* (2013.01)

(56) References Cited

U.S. PATENT DOCUMENTS

2002/0068948 A1* 6/2002 Stormby .......... A61B 17/06109
                                                            606/151
2012/0232573 A1* 9/2012 Ostrovsky .......... A61B 17/0482
                                                            606/185

FOREIGN PATENT DOCUMENTS

WO    2012/122476 A2    9/2012
WO    2014/138107 A2    9/2014

OTHER PUBLICATIONS

International Preliminary Report on Patentability for PCT Patent Application No. PCT/US2014/020387, mailed on Sep. 17, 2015, 9 pages.
International Search Report and Written Opinion for PCT Patent Application No. PCT/US2014/020387, mailed on Sep. 23, 2014, 13 pages.

* cited by examiner

MEDICAL DEVICES AND IMPLANT ASSEMBLIES FOR IMPLANT CAPTURE

CROSS-REFERENCE TO RELATED APPLICATIONS

This application is a Nonprovisional of, and claims priority to, U.S. patent application No. 61/773,972, filed on Mar. 7, 2013, entitled "MEDICAL DEVICES AND IMPLANT ASSEMBLIES FOR IMPLANT CAPTURE", which is incorporated by reference herein in its entirety.

This application is related to co-owned and co-assigned U.S. Provisional Application No. 61/773,966, filed on Mar. 7, 2013, entitled "DEVICES FOR DELIVERING IMPLANTS," and U.S. application Ser. No. 13/416,488, filed on Mar. 9, 2012, entitled "MULTI-ARM INSIDE-OUT TOOL FOR DELIVERING IMPLANTS AND METHODS THEREOF", and U.S. application Ser. No. 13/598,143, filed on Aug. 29, 2012, entitled "A MULTI-ARM TOOL FOR DELIVERING IMPLANTS AND METHODS THEREOF". The entirety of each of these related applications is incorporated by reference herein.

TECHNICAL FIELD

This invention generally relates to implants and medical devices that are configured to position implants within the body of a patient.

BACKGROUND

Urinary incontinence, or loss of bladder control, is a condition that causes people to involuntarily leak urine while coughing, sneezing, laughing, and exercising. Men and women both suffer from incontinence. Almost 16 percent of the women population suffers from urinary incontinence, and men account for a quarter the total patient population.

Typically, urinary incontinence is treated by placing a supportive implant, often called a sling, into the pelvic region of a patient. The supportive implant is used to cradle or support the bladder or urethra, depending on the procedure. Supportive implants are delivered to the pelvic region through one or more vaginal incisions and/or through exterior incisions in body of the patient. In addition to urinary incontinence, supportive implants placed into the pelvic region can also be used to correct various pelvic prolapse conditions, which include uterine prolapse, rectocele, cystocele, and urethrocele.

The common procedure for delivering such implants into the pelvic region of the patient involves a delivery tool that has a long curved shaft with a hooked needle tip attached to a handle. A surgeon maneuvers by hand the delivery tool into and within the pelvic region through and/or around tissue where the implant is desired to be placed. Once positioned, the surgeon must further manipulate the delivery tool by hand to capture an implant attached to a looped end onto the hooked needle tip. In some instances, the surgeon may require an additional tool to grasp the implant and place the implant onto the hooked needle tip. After which, the surgeon withdraws the delivery tool to position the implant in the desired location.

The above procedure is limited because it requires direct vision of the surgeon to capture the implant in sometime hard to access regions of the pelvic. In addition, the delivery tool is hard to control by hand, and often the delivery tool deviates from the desired path of implantation. This deviation can result in failed attempts to capture the implant and to improper placement of the implant. Moreover, deviation of the delivery tool can result in inadvertent tissue, nerve, bladder, or urethral damage, and any required additional attempts at implant delivery significantly increase the risk of such tissue and/or nerve damage.

SUMMARY

Devices and methods of the invention allow an operator to position an implant into the body of a patient without the need for direct-vision of the operator or the need to hand-guide a needle in order to capture an implant. The invention includes multi-arm delivery devices, implants and implants assemblies, and methods for blind-capture of the implants with the multi arm delivery device. In one aspect, the multi-arm delivery device includes a receiving arm that releasably holds an implant in place for capture and a clamping arm that includes a needle deployment mechanism for advancing a needle directly to the releasably-held implant for capture and for retracting the needle with the implant attached to deliver the implant into the desired location. Because the multiarm delivery device does not require the operator to hand guide the needle, the device significantly lessens inadvertent tissue damaged caused by needle deviation. In addition, the multi-arm delivery device advantageously allows one to pre-position the implant into the body. Once pre-positioned, the device guides the needle through the desired implantation location directly to the implant for capture, and then the pulls the implant to the desired location. This diminishes the risk of improper placement of the implant and increases successful capture events.

In addition, the inventors realized that the needle path may minutely deviate despite being directed by the multi-arm delivery device due to the densely-packed tissue in the pelvic region. Such minute deviations are not likely to cause damage, but the deviations may result in a failure to capture the implant. For example, if the implant is attached to a single suture loop and the needle includes one retaining slot, the needle deployment mechanism must precisely position the needle so that the single suture loop is placed into the retaining slot of the needle. If the needle path deviates so that the needle goes slightly under or below the suture loop, the suture loop may not be placed in the needle retaining slot.

To account for such minute deviations in the needle path and to prevent any potential failed implant capture, the invention provides for use of needles with multiple retaining slots and/or implant assemblies including multiple capture portions. The combination of the multi-arm delivery with the needle having multiple retaining slots and/or implant assemblies with multiple capture portions significantly expands the acceptable range of the delivery path of the needle and increases the probability that the implant will be captured by the needle. This provides for implant capture regardless of slight deviation of the needle.

According to certain aspects, a multi-arm delivery device includes a first portion and a second portion coupled to the first portion. The first portion of the delivery device includes a handle, a junction section, and a needle-receiving arm extending distally from the junction section. A distal portion of the needle receiving-arm is configured to releasably-hold an end portion of an implant. The distal portion defines an opening that leads to a cavity for receiving a needle comprising a plurality of retaining slots. The implant end portion is releasably held within the cavity. The second portion of the multi-arm delivery device includes a clamping arm movably coupled to the junction section of the first portion.

The clamping arm allows an operator of the delivery device to hold the handle and move the clamping arm with respect to the first portion. In one embodiment, the clamping arm is curved. The clamping arm includes a needle deployment mechanism for advancing the needle comprising a plurality of retaining slots through tissue of the body of the patient and into the cavity of the distal portion of the needle-receiving arm. The needle deployment mechanism is configured to direct the needle towards the receiving arm. As the needle is advanced into the cavity, at least a portion of the implant end portion is placed into at least one of the plurality of needle retaining slots. The needle deployment mechanism also retracts the advanced needle out of the cavity and back through the tissue to pull the end portion of the implant through tissue for positioning.

Embodiments according to this aspect of the invention can include various features. In one embodiment, the needle deployment mechanism of the clamping arm has a distal end and a proximal end and includes a sliding component coupled to the needle. The sliding component can be slideably disposed on a guide rail such that movement of the sliding component in the distal direction along the guide rail advances the needle to the receiving arm and movement of the sliding component in the proximal direction along the guide rail retracts the needle. The guide rail can be straight or curved. In an embodiment, the guide rail conforms to the shape or curvature of at least a portion of the clamping arm. The needle can include one or more retaining slots. The retaining slots can be located on the distal end of the needle and configured to capture the end portion of the implant when the needle retracts from the cavity of the needle-receiving arm. The retaining slots can be arranged around the same cross-section of the needle, spirally-aligned on the needle, located distal to one and other, or arranged in any other orientation. In addition, the needle can be straight or curved. For example, the needle can conform to the shape or curvature of the at least a portion of the clamping arm or at least a portion of the guide rail. The implant end portion can include a mesh catch for receiving the needle. The mesh catch may include a plurality of openings. Each of the plurality of openings of the mesh catch can be defined by at least one flexible edge configured to move. During capture, at least one of the flexible edges moves as the needle advances into one of the plurality of openings of the mesh catch, and this at least one of the flexible edge moves into at least one retaining slot as the needle is retracted. The mesh catch can be formed as part of the implant or coupled to the implant via a suture. The implant end portion can include a bundled catch for receiving the needle. The bundled catch can define a volume. The bundled catch can comprise a plurality of flexible members spherically disposed between two suture arms for receiving a needle. Alternatively, the bundled catch can comprise a plurality of looped members for receiving the needle, or the bundled catch can be a netted or threaded ball. The bundle catch can be coupled to at least one suture arm. During capture with the bundle catch, at least a portion of the advancing needle enters into the bundled catch, and a portion of the bundle catch is configured to enter one or more retaining slots as the advanced needle retracts.

Although the multi-arm delivery device is suitable for delivering any type of implant, in certain aspects, the implant is a sling for implantation into the body of the patient to treat urinary incontinence by raising or supporting the patient's bladder neck. The implant may also be a mesh implant used to correct various pelvic prolapse conditions, which include uterine prolapse, rectocele, cystocele, and urethrocele. The implant also includes an end portion (also referred to herein as the capture portion) for receiving a needle. The capture portion of the implant can be formed as part of the implant or can be coupled to or attached to the implant. For example, the capture portion can be coupled to the implant via a connecting element (e.g. a suture). Because certain embodiments of the implant include a sling and a capture portion, the implant is also referred to as an implant assembly. In some embodiments, the capture portion is detachable from the sling after the sling is positioned within the body of the patient. In certain embodiments, the implant is contained within a packaging, and the end portion or capture portion extends from the packaging. In another aspect, the invention relates to an implant assembly for treating urinary incontinence in a patient. The implant assembly includes a sling configured for implantation into the body of the patient the patient for raising or supporting the patient's bladder, bladder neck or urethra, and a capture portion coupled to the sling and configured to receive at least portion of a needle comprising one or more retaining slots into the capture portion. At least a part of the capture portion configured to be retained in the one or more retaining slots to allow the needle to position the sling into the body of the patient. Embodiments according to this other aspect of the invention also can include various features. In certain embodiments, the capture portion of an implant assembly is coupled to a suture that attaches the capture portion to a sling. The suture can directly attach to the capture portion, or the suture can include two or more suture arms that attach to the capture portion. The suture and/or suture arms assist in positioning and releasably holding the capture portion in the cavity of the receiving arm. For example, the distal end of the receiving arm can have one or more slits, and the suture or suture arms are positioned within the slits to place the capture portion within the cavity.

In certain embodiments, the capture portion is a mesh catch comprising a plurality of openings for receiving the advanced needle. Each of the plurality of mesh openings can be defined by at least one flexible edge of the mesh catch. As the needle passes into one of the plurality of openings in the mesh catch, at least one of the flexible edges of this opening moves to receive the needle and then moves again into a retaining slot of the needle. When the needle retracts, the flexible edge remains in the retaining slot, and the needle pulls the implant into the desired position in the body. In other embodiments, the capture portion is a bundled catch that is configured to receive at least a portion of the needle into the bundle catch and at least a portion of the bundled catch is configured to enter one or more retaining slots of the needle. The bundle catch can be a three-dimensional catch defining a volume that includes a plurality of capture members. The plurality of capture members increase the likelihood that a portion of the bundle catch will enter and be retained in one or more retaining slots of a needle. In one embodiment, the bundle catch is a plurality of looped members. In another embodiment, the bundle catch is a threaded or netted ball. In yet another embodiment, the bundled catch is a plurality of flexible members spherically disposed between two suture arms.

Other and further aspects and features of the invention will be evident from the following detailed description and accompanying drawings, which are intended to illustrate, not limit, the invention.

BRIEF DESCRIPTION OF THE DRAWINGS

FIG. 13b depicts a close-up view of the mesh catch in FIG. 13a.

FIG. 14b depicts a close-up view of the bundled catch of FIG. 14a.

FIG. 15b depicts a close-up view of the bundled catch of FIG. 15a.

DETAILED DESCRIPTION

The invention relates to multi-arm delivery devices, implants and implant assemblies, and method of using the device for inserting and placing implants or implant assemblies within a body of the patient. The multi-arm tool is suitable for delivering implants into any portion of the body. Particularly, the multi-arm delivery device is for inserting and placing supportive implants into the pelvic region of a patient. Once the multi-arm delivery device places an implant into the desired location within the pelvic region of the patient, the implant can be secured to the pelvic wall or surrounding tissue to provide required support for treatment.

Typically, the supportive implants are positioned with the multi-tool delivery device for the treatment of urological disorders, such as stress incontinence, urge incontinence, mixed incontinence, overflow incontinence, prolapse (e.g. vaginal), enteroceles (e.g. of the uterus), rectoceles and other non-urological disorders, are also included within the scope of the present invention. The multi-arm delivery device is also suitable for delivering implants in procedures to treat, for example, cystocele prolapse, other types of vaginal prolapse and anatomic hypermobility.

Various embodiments of the multi-arm delivery device, methods of use, and implants assemblies for use with the multi-arm delivery device are described hereinafter. The various implant assemblies can be used in combination with any one of the embodiments of the multi-arm delivery device without limitation. In addition to use in combination with the multi-arm delivery device of the invention, the implant assemblies and implants may also be used in conjunction with any other implant delivery devices.

Figure 1:
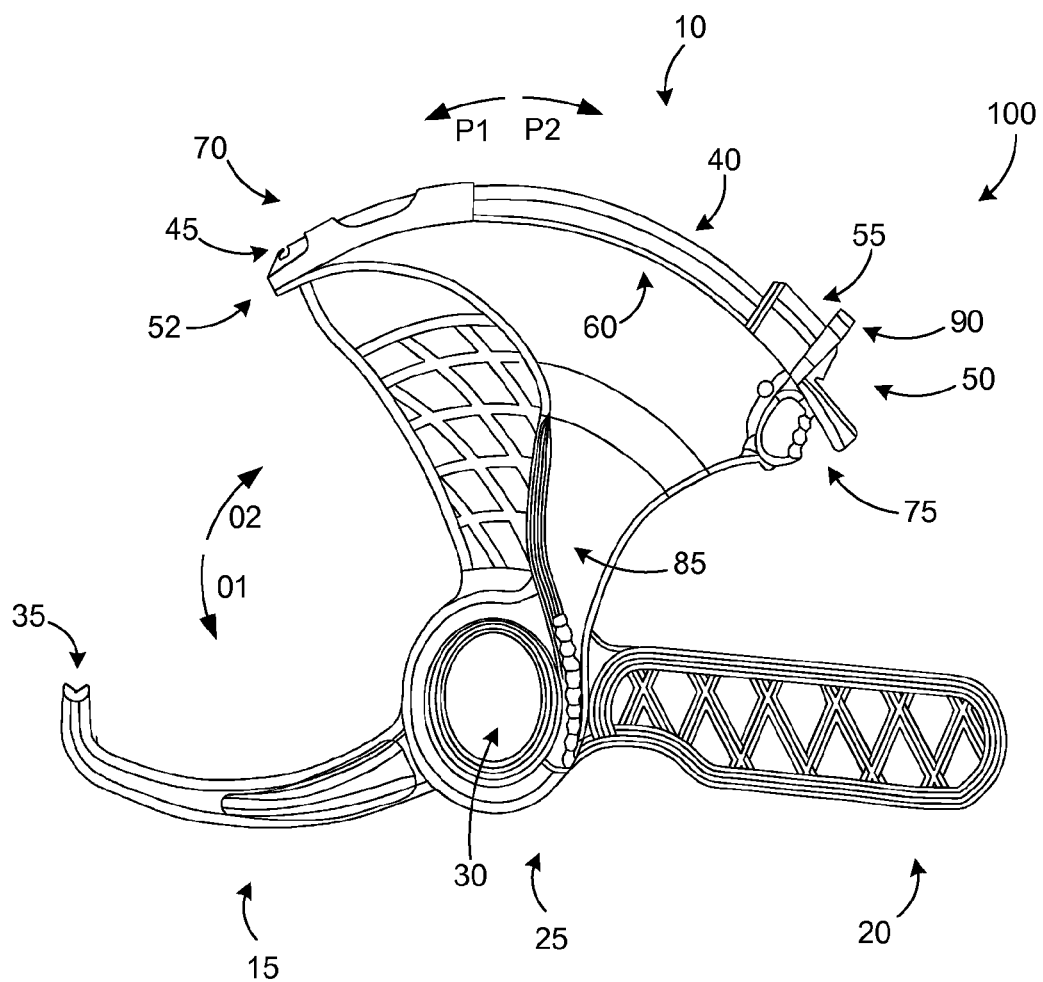
FIG. 1 depicts an embodiment of the multi-arm delivery device.

FIG. 1 depicts an embodiment of the multi-arm delivery device 100. The multi-arm delivery device 100 includes a clamping arm 10 and a receiving arm 15. The receiving arm 15 extends distally from a junction section 25 which extends distally from a handle 20. The clamping arm 10 is movably coupled to the junction section 25. In addition, the receiving arm 25 can be movably coupled to the junction section 25. The clamping arm 15 typically has an L-like shape or T-like shape, and a portion of the clamping arm 10 can be curved or straight. The clamping arm 10, as shown in FIG. 1, includes a curved portion. The curvature of the clamping arm 10 is designed to deliver the needle directly into a cavity of the distal end of the receiving arm 15.

The junction section 25, as shown in FIG. 1, includes a finger hole 30 that can be used to grasp the delivery device 100 along with the handle 20. The junction section 25 also operates as a hinge to allow movement of the clamping arm 10 with respect to the receiving arm 15, or vice versa. The clamping arm 10 is rotatably movable in the direction O1 and/or the direction O2 with respect to the receiving arm 15. Alternatively, the receiving arm 15 is rotatably movable in the direction O1 and/or the direction O2 with respect to the clamping arm 10.

Figure 2:
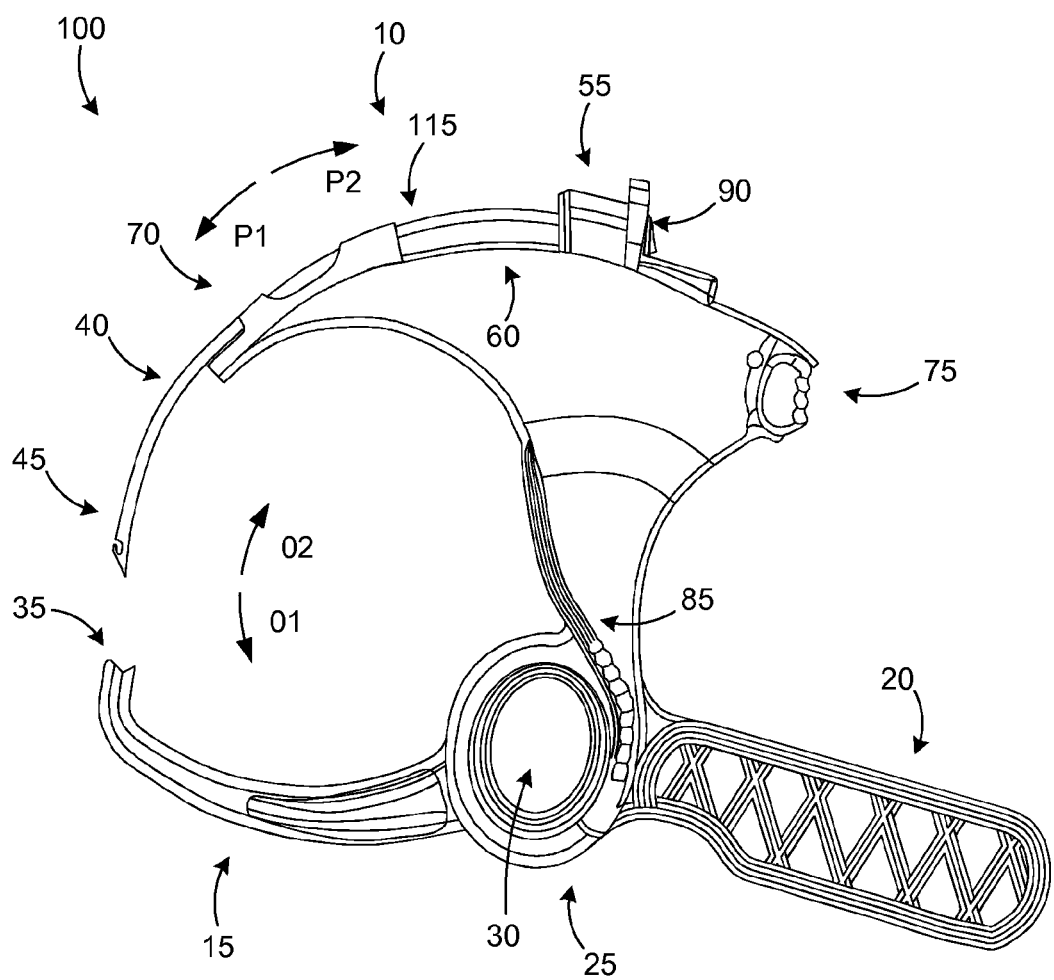
FIG. 2 depicts an embodiment of the multi-arm delivery device with the clamping arm moved towards the receiving arm and the needle advanced towards the receiving arm.
Figure 4:
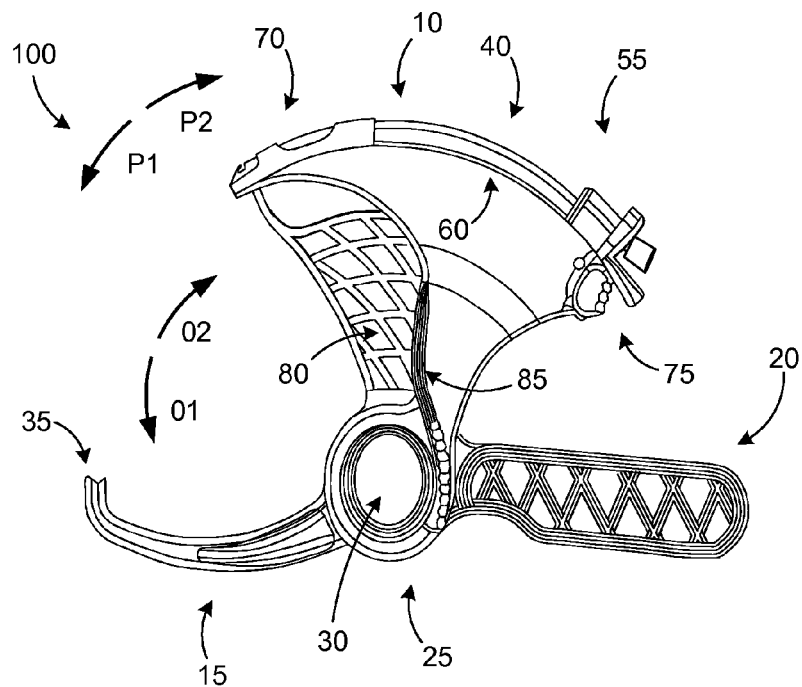
FIG. 4 depicts the multi-arm delivery device in an open configuration.
Figure 5:
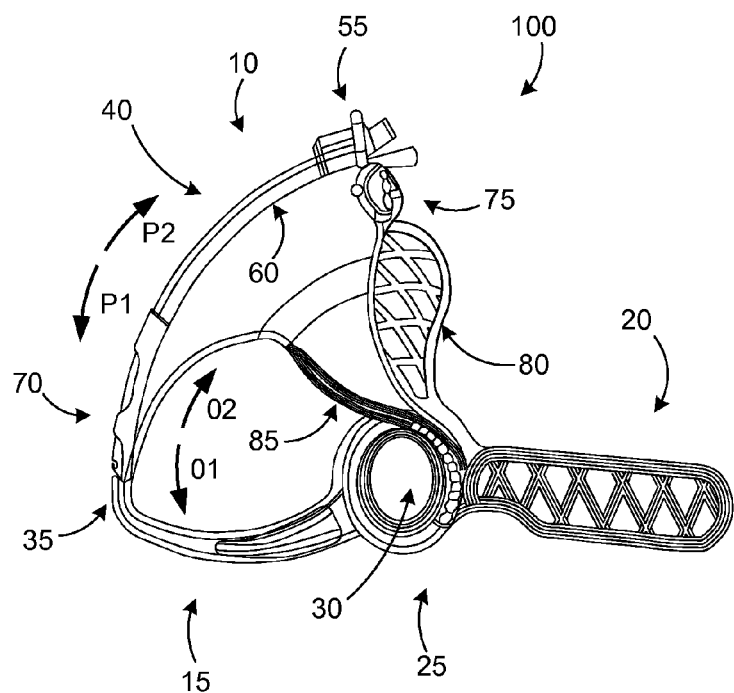
FIG. 5 depicts the multi-arm delivery device in a closed configuration.

FIG. 4 shows the multi-arm delivery device in an open configuration with the clamping 10 moved away from the receiving arm 15. FIG. 5 shows the clamping arm 10 in a completely clamped configuration, i.e. moved all the way towards the receiving arm 15 in the O1 direction. FIG. 2 shows the clamping arm 10 is a partially clamped configuration. The desired clamped configuration for a procedure will depend on the amount of tissue between the receiving arm 15 and clamping arm 10 and the type of procedure.

Figure 3:
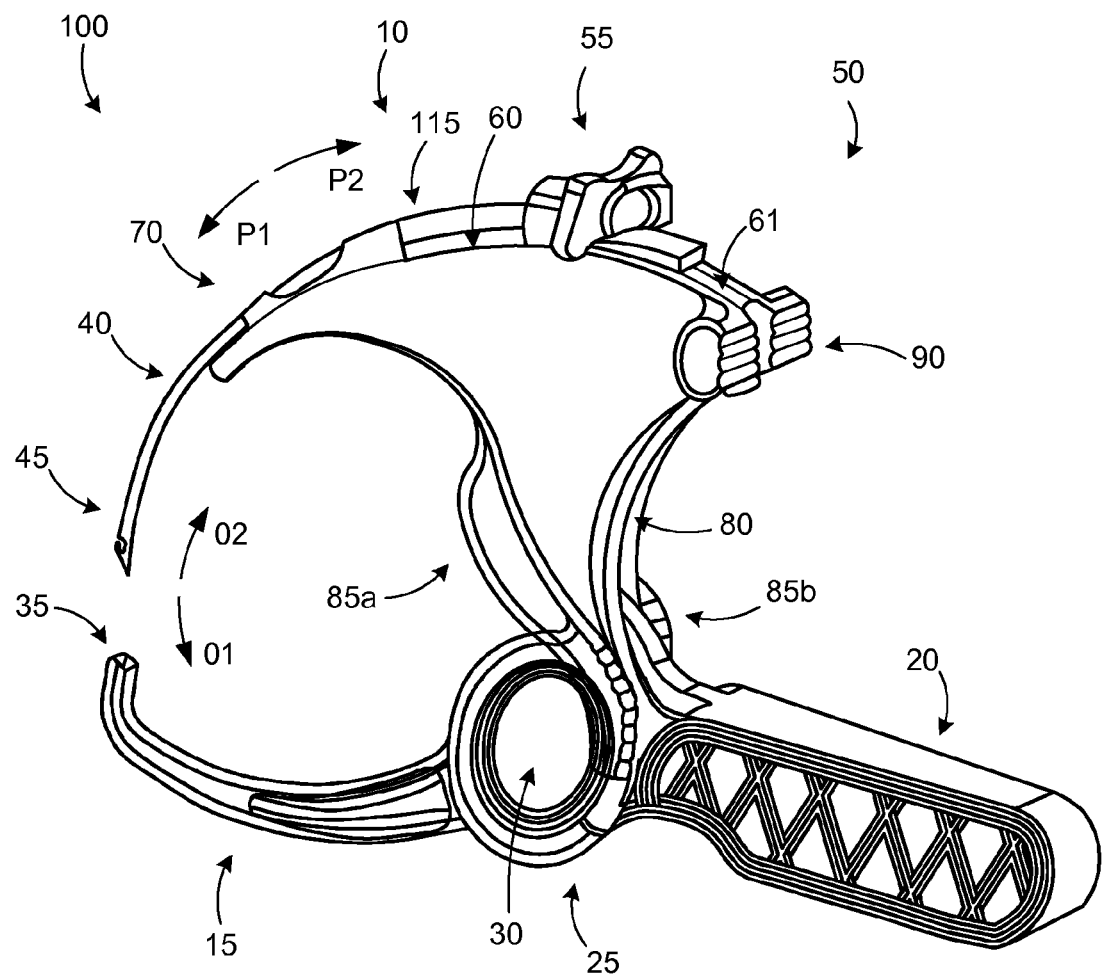
FIG. 3 depicts an angled view of FIG. 2.

The multi-arm delivery device 100 as shown in FIGS. 1-5 includes inner guide 80. The inner guide 80 is an optional element that is fixed to junction section 25 and disposed within the clamping arm 10. The inner guide 80 can be used as an additional gripping element for the operator, and acts to stabilize and direct the clamping arm towards the receiving arm. The clamping arm 10 slideably moves over the inner guide 10 in the O1 direction and O2 direction. When the device is in the open configuration as shown in FIG. 4, the inner guide 80 is shown in the open space between the clamping arm 10 and the receiving arm 15. FIGS. 2 and 3 show the clamping arm 10 in a partially clamped position in which the inner guide 117 is completely disposed within the clamping arm 10. FIG. 4 shows the clamping arm 10 in a fully clamped position with the inner guide extending behind the clamping arm 10.

The clamping arm 10 includes one or more side tabs 85 along the side of the clamping arm 10. The side tabs 85 include a smooth portion 85a and rough portion 85b. The side tabs 85 are best shown in FIG. 3, which provides an angled view of multi-arm delivery device 100. The side tabs 85 can be used by an operator to push (e.g. using a thumb) the clamping arm 10 towards the receiving arm 15 in the O1 direction. The side tabs 85 can also be pulled on by an operator to move the clamping arm in the O2 direction. The side tabs 85 can be used to hold the device 100 in a clamped configuration. For example, the operator can hold the device 100 in a clamped configuration prior to operating the needle deployment mechanism of the clamping arm, which is described more detail below. The smooth portion 85a is configured so that a thumb of an operator can slide along the smooth portion 85a to move the clamping arm 10 towards the receiving arm 15. The rough portion 85b is configured to stop the sliding of the operator's thumb and the rough portion 85b acts as a grip. The rough portion 85b can have any suitable friction-based surface, such as a rough adhesive surface, sandpaper-type surface or a bumpy surface. As shown in FIGS. 1-5, the clamping arm 10 also includes one or more finger tabs 75 that can also be used by an operator to push the clamping arm 10 in the O1 direction and pull the clamping arm in the O2 direction. The finger tabs 75 can include any shape suitable for pushing and pulling the clamping arm 10. As shown, the finger tabs 75 have a rough surface for pushing and the finger tabs form an finger hole in the clamping arm 10 that allows an operator to insert a finger to pull the clamping arm 10.

In certain aspects, the multi-arm delivery device 100 includes a biasing mechanism such as a spring, ratchet or gear that biases the clamping arm 10, for example, in the open configuration shown in FIG. 4 or the clamped configuration FIG. 5. The biasing mechanism automatically moves the clamping arm 10 towards the biased position upon removal of operator applied force. In some aspects, medical device 100 can include a locking element on the clamping arm 10 that locks the clamping arm in a specific position. The clamping arm 10 of the medical device 100 can be configured to be fixed at any location along the direction O1 by the locking mechanism. The locking mechanism can include a ratchet mechanism.

The distal end of the clamping arm 10, as shown in FIG. 1, includes a needle deployment mechanism that includes a proximal portion 50 and a distal portion 52. The needle deployment mechanism is used to advance the needle 40 through tissue towards the receiving arm 15 to capture an implant 165, and is also used to retract the needle 40 back through the tissue while pulling the captured implant 165 into position.

The needle deployment mechanism includes a sliding component 55 and a guide rail 60. The guide rail 60 can be curved or straight, but is shown in FIGS. 1-5 as curved. In some embodiments, the shapes of the guide rail 60 and the needle 40 are dependent on the curvature or shape of the clamping arm 10. The guide rail 60 includes a groove 61 (shown in FIG. 3) that allows the sliding component 55 to slidably move within the groove 61 in direction P1 and in direction P2. The sliding component 55 is operably coupled to the needle 40, and movement of the sliding component 55 allows for the needle to be advanced and refracted. As the sliding component moves in direction P1, the needle is advanced towards the receiving arm 15. FIGS. 3 and 4 show the sliding component moved towards the distal portion of the needle deployment mechanism 52 with the needle 40 advanced halfway across an open space between the receiving arm 15 and clamping arm 10. During a procedure, the needle 40 would pass through or around tissue disposed within the open space.

The sliding component 55 includes a grip 90 that allows the operator to push and pull the sliding component along the guide rail 60 in order to deploy and retract the needle. The grip 90 can be made in any shape or size that is convenient to the operator. As shown in FIGS. 1-5, the grip 90 is a tab structure. Alternatively, the grip 90 can made into a handle or configured to receive and retain a detachable handle. In one aspect, the grip is configured to receive and attach to a syringe, and the syringe can be used to move the sliding component 55 and deliver drugs through the needle and into tissue of the patient while the needle is advanced and retracted through tissue. In such embodiment, the needle 40 defines a lumen for transmitting the drug delivered into the needle by the syringe.

In certain aspects, the needle deployment mechanism includes a biasing mechanism that causes the sliding component 55 to be biased to the stowed configurations (i.e. when the needle is retracted) as shown in FIGS. 1, 4 and 5, or alternatively, in a deployed configuration (i.e. when the needle is advanced) as shown in FIGS. 2 and 3. Although not shown, the biasing mechanism can be a spring disposed within the groove 61 of the guide rail 60. When force is no longer applied to the sliding component in the P1 direction, the spring automatically pushes the sliding component in the P2 direction towards the proximal portion of the needle deployment mechanism 50. In some embodiments, the needle deployment mechanism can include at least one of a piston, a spring, an actuator, and the like mechanism to make the sliding component 55 movable.

The sliding component 55 can move independently from the clamping arm 10, and the clamping arm 10 can move independently from the sliding component 55. For example, during a procedure, the operator can, without moving the sliding component, clamp down the tissue through which the implant will be placed by moving the clamping arm in the O1 direction towards the receiving arm with the tissue disposed between the arms. With the tissue clamped and the clamping arm held in the clamped position, the operator can then move the sliding component in the P1 direction towards the receiving arm 15 to capture the implant 165.

Figure 8A:
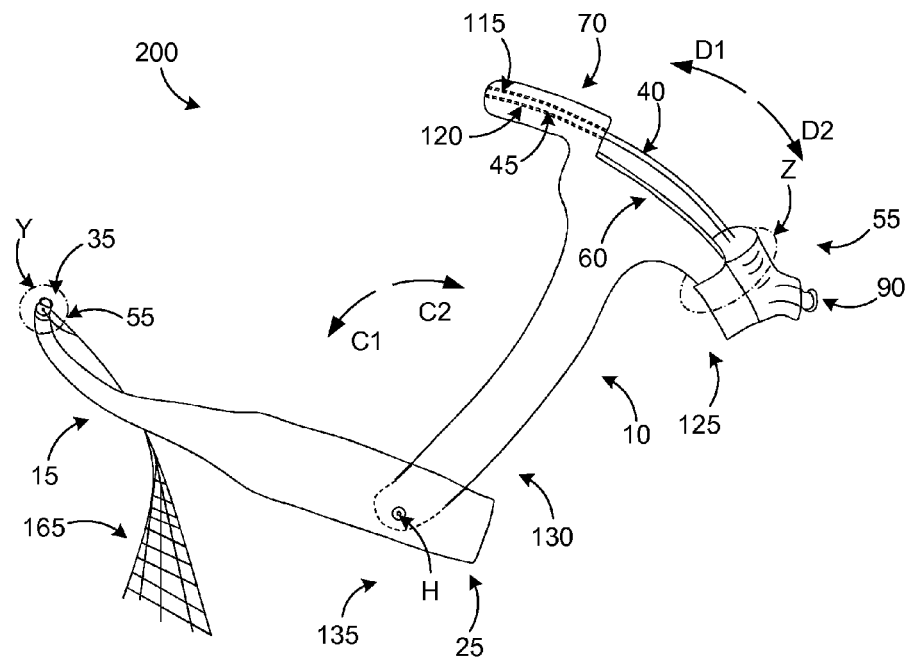
FIGS. 8a-8c illustrate the multi-arm delivery device in various positions of operation.
Figure 8B:
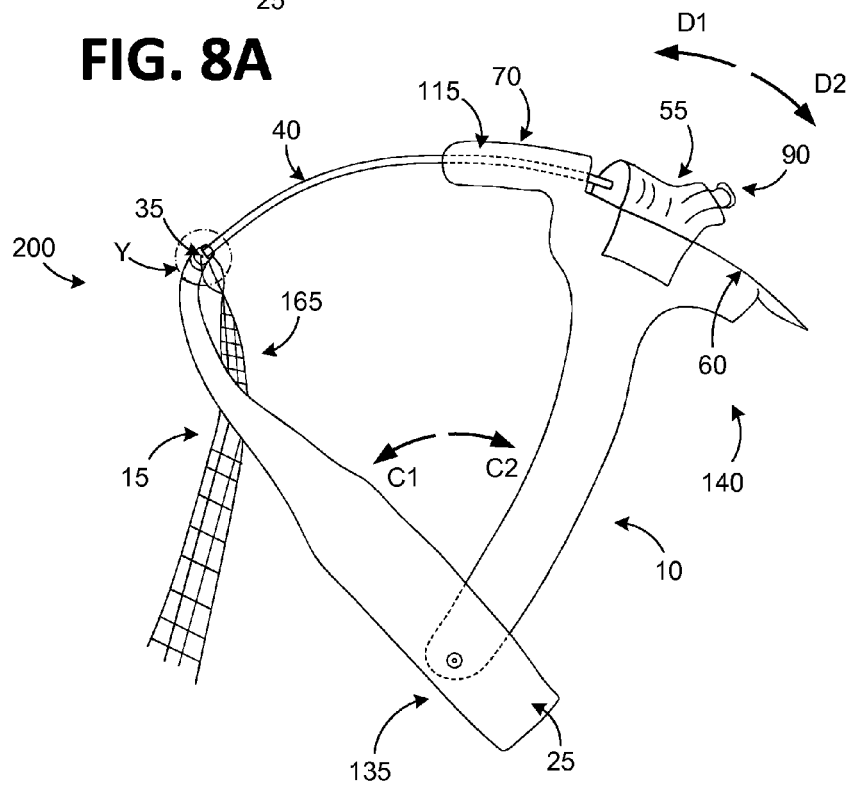
Figure 8C:
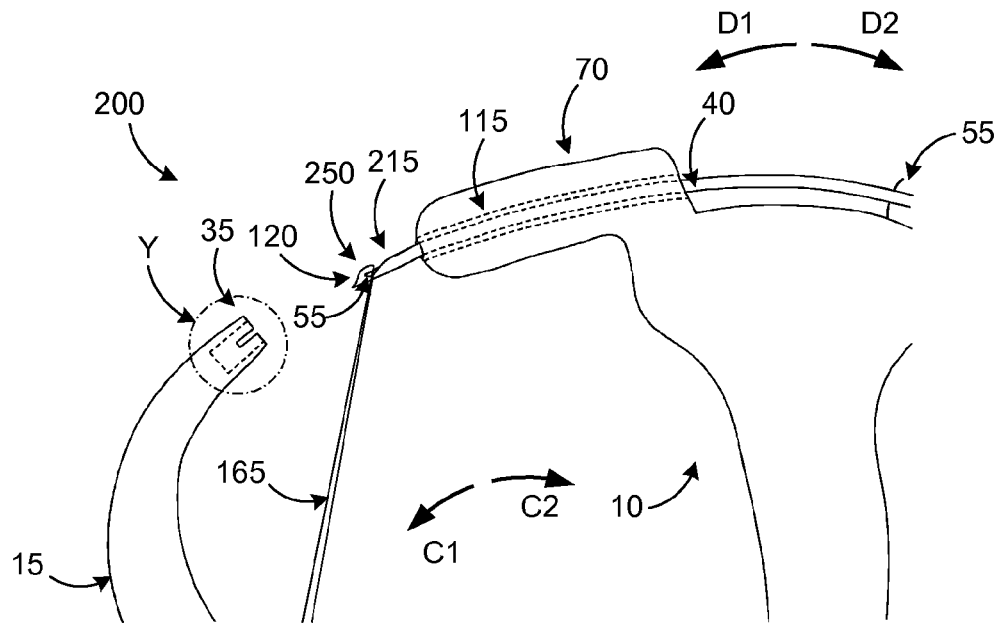

As shown in at least FIG. 1, a guide compartment 70 is disposed on the distal portion 52 of the needle deployment mechanism. The guide compartment 70 defines at least one lumen 115 through which the needle 40 passes during deployment and retraction. As shown in FIG. 1-5, the guide compartment includes two sections and defines two lumens. FIGS. 8a-8c show a guide compartment 70 with only one section that defines one lumen. The guide compartment 70 also houses or stows the needle 40 prior to deployment, as shown in FIGS. 1, 4 and 5. The guide compartment 70 acts to direct the advancing needle 40 with little to no deviation towards the receiving arm 15.

The receiving arm 15 is configured to releasably hold a capture portion 55 of an implant assembly (i.e. the end portion of an implant) in the distal end 35 of the receiving arm 15. The distal end 35 of the receiving arm 15 is best shown in FIGS. 13c and 15c. As shown in FIG. 13c, the distal end 35 of the receiving arm 15 includes an opening 237 leading to a cavity 240. The distal end 35 of the receiving arm contains one or more slits 145 for releasably holding the capture portion within the cavity 240. In FIG. 13c, the distal end 35 includes two slits 145 for releasably holding a mesh capture portion 185 that is coupled to two arms of a suture 205. In FIG. 15c, the distal end 35 includes one slit 145 for releasably holding a bundled capture portion 400 that is directly coupled to a suture 205.

Although the needle 40, as shown in FIGS. 1-5, includes a single retaining slot 215 located on the distal end 45 of the needle 40, in preferred aspects of the invention, the needle includes a plurality of retaining slots 215. The needles 40 with a plurality of retaining slots are shown in FIGS. 12a-12d and are described hereinafter.

In an embodiment, the medical device 100, can be made of ultra violet (UV) cured epoxy resin. In some embodiments, the UV cured epoxy resin can be fabricated by Stereo Lithography Apparatus (SLA). In some embodiments, various components of the medical device 100 can be made of any plastic or metal (such as polycarbonate or 304 stainless steel) materials. Other embodiments may include use of manufacturing methods including but not limited to molding or machining components and materials including but not limited to metals, polymers and ceramics.

The multi-arm delivery device can be used to place supportive implants into the various positions within pelvic region for treatment of incontinence and to correct various pelvic prolapse conditions such as uterine prolapse, rectocele, cystocele, and urethrocele.

The supportive implants, typically called slings, include posterior support implants, anterior support implants, and or total pelvic floor repair implants. The implants are used to treat a variety of pelvic dysfunctions and can be placed and secured at various locations within the pelvic space for treatment. For example, an implant can be secured to a sacrospinous ligament or an ureterosacral ligament for posterior support or for uterine preservation. A uterine preservation procedure is performed, instead of a hysterectomy, when the prolapsed uterus is otherwise healthy and can maintain normal function if re-suspended by an implant. Posterior support is used to treat posterior vaginal wall prolapse, also called "rectocele," that is caused by a weakening of the wall between the vagina and the rectum. Implants can also be placed for securing the implant to the pubo-urethral tissue or an obturator muscle (e.g. internus or externus) and/or obturator membrane to treat, for example, incontinence. An implant can also be secured to a sacrospinous ligament or an arcus tendineus fascia pelvis (also known as "arcus tendineus) for paravaginal repairs. Paravaginal repairs include cystoceles, rectoceles, and enteroceles.

Patients that undergo implant procedures include both male and female patients. A patient may have one or multiple implants inserted at a time. For example, an implant procedure may include securing an implant to the sacrospinus ligament and securing an implant to the pubo-urethal tissue.

Because different procedures and different treatments require different implant positions, the multi-arm delivery device provides for implant delivery through a variety of incisions sites into the body. For example, the multi-arm delivery device can be used to position an implant through a vaginal incision, in a retro-pubic direction (i.e. behind the pubic bone), in a pre-pubic direction (i.e. in front of the pubic bone), or in a supra-pubic direction (above the pubic bone). The multi-arm delivery device can also be used to places an implant through or around any anatomical tissues or ligaments disposed within the pelvic region. Types of vaginal incisions through which the multiarm delivery tool place implants include anterior vaginal incisions and/or posterior vaginal incisions. In addition, the multi-arm delivery tool can also be used to deliver implants through an exterior incision.

Figure 6A:
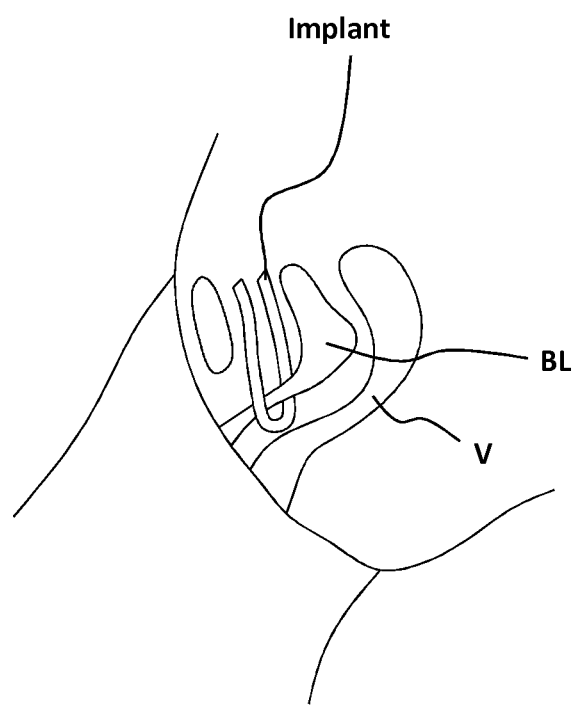
FIGS. 6a-6c illustrate the pelvic region of a patient and various implant locations.
Figure 6B:
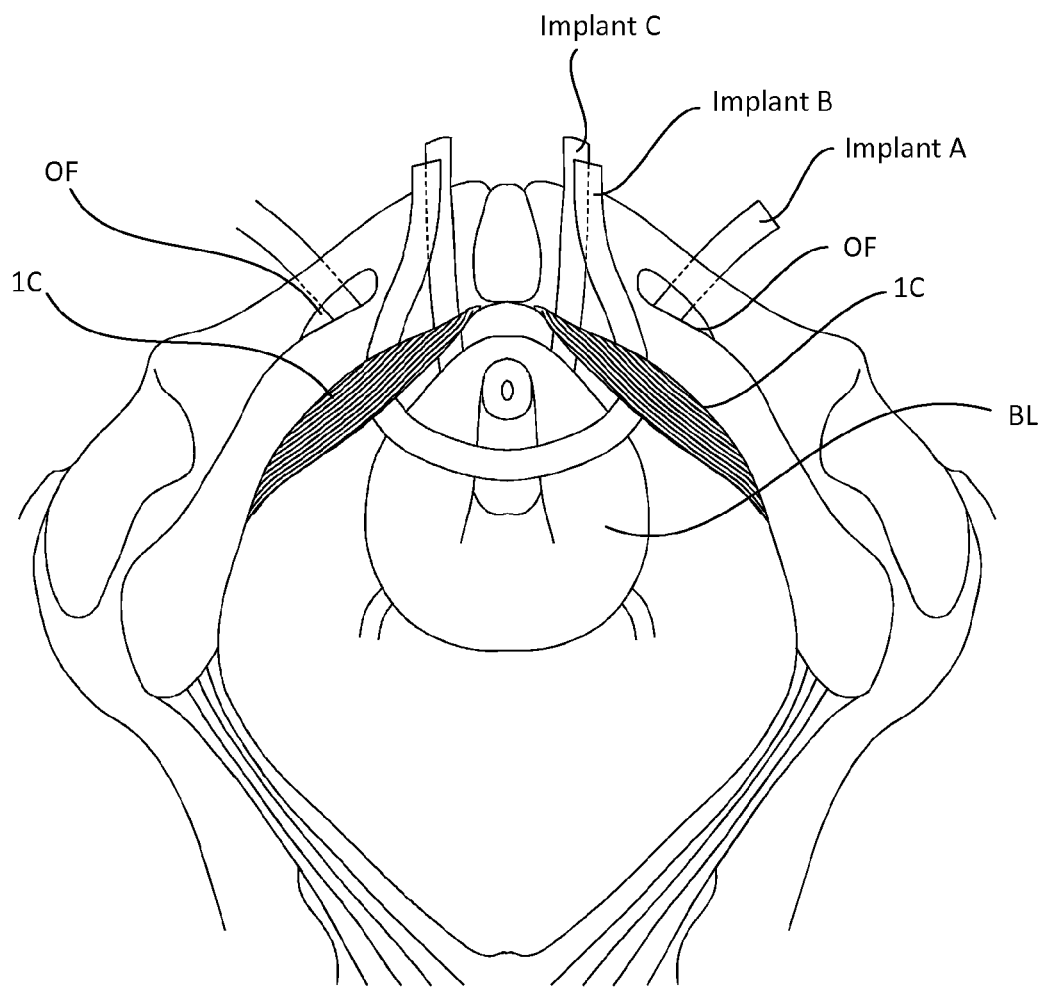
Figure 6C:
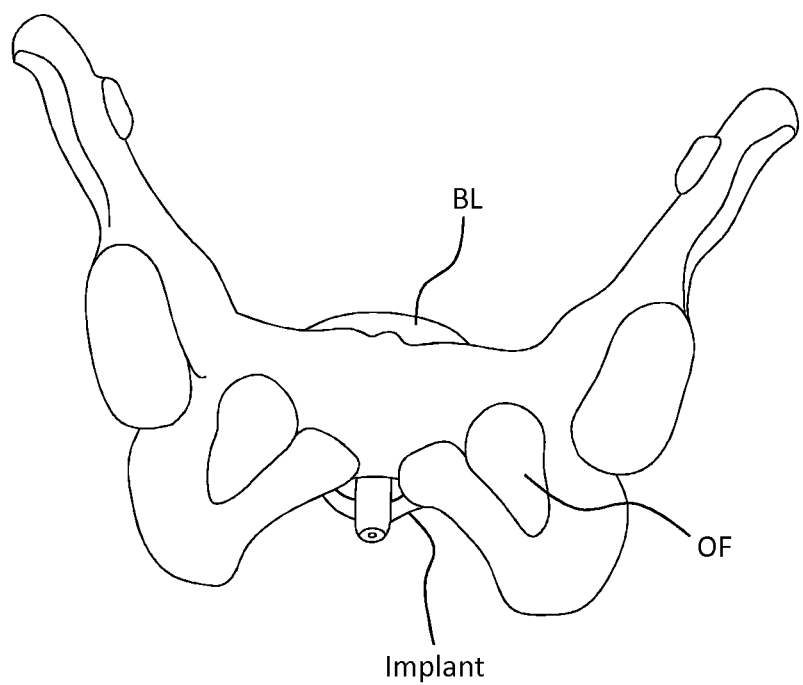

FIGS. 6a-6c depict the various implant locations that the multi-arm delivery device 100 can be used for positioning or delivering the implant to the location. The various implant locations illustrated in FIGS. 6a-6b are not exhaustive, but rather shown to exemplify some of the many positions that the multi-arm delivery device 100 can place implants.

FIG. 6a illustrates an implant positioned between a portion of a vagina V of a patient and a portion of a bladder BL of the patient so that the implant provides support to the bladder BL of the patient.

FIG. 6b illustrates an implant A positioned into the body so that the implant A extends through the patient's obturator foramens OF. In addition, FIG. 6b illustrates an implant B positioned between the midline incision, the Ischiocavernosus muscle IC, and in front of the pubic bone. In order to position implant B, the multi-arm delivery device would enter the pelvic region from a pre-pubic direction. Although not shown, Implant B can also be extended between the arcus tendineus facia pelvis (ATFP) and the obturators OF. FIG. 6b also illustrates implant C positioned in a "V" shape under the bladder and in front of the Ischiocavernosus muscle IC.

FIG. 6c illustrates an implant positioned so that the implant extends towards the obturator foramens OF but does not extend through the obturator foramens OF. In this position, the implant may be disposed within or coupled to muscles that are proximate to the obturator foramens OF.

Figure 7:
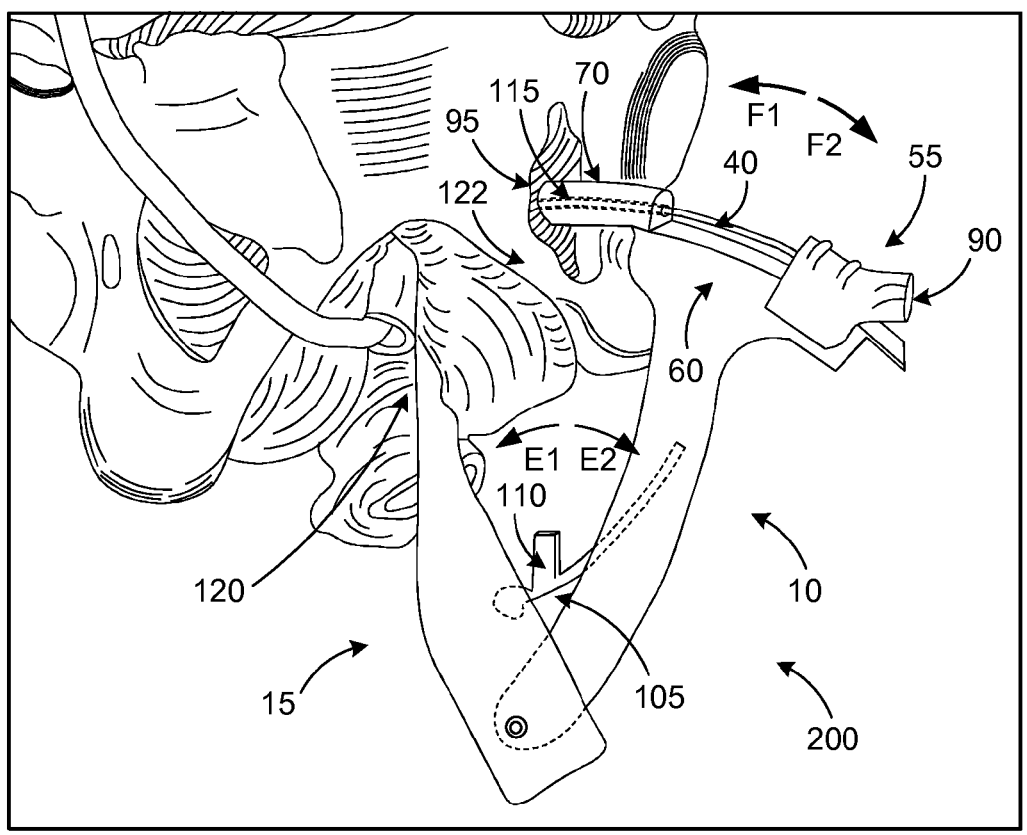
FIG. 7 depicts an embodiment of the multi-arm delivery device in use within the body of a patient.

FIG. 7 shows an embodiment of the multi-arm delivery device 200 in use within the body of a patient. As shown in FIG. 7, at least a portion of the receiving arm 15 is disposed within the vaginal region 120 of the patient. The clamping arm 10 is pressed against the tissue 122 between the receiving arm 15 and the clamping arm 10. The guide compartment 70 is pressed against the obturator foramens 95 of the patient. The sliding component 55 is deployed in the F1 direction so that at least a portion of the needle 40 is pushed through the lumen 115 of the guide compartment 70 and into the tissue 122. The multi-arm delivery device 200 includes a locking mechanism 105. The locking mechanism 105 rotatably couples to the receiving arm 15 and engages with the clamping arm 10. The locking mechanism 105 includes a finger tab 110, which may be used to adjust the locking mechanism 105. The locking mechanism 105 may include a ratchet mechanism.

FIGS. 8a-8c illustrate the multi-arm delivery device 200 in various positions of operation. As shown in FIG. 8a, the multi-arm delivery device 200 includes a receiving arm 15 and a clamping arm 10 rotatably coupled to receiving arm at junction 25. The junction 25 includes a hinge H (e.g. coupled via a pin, screw, etc.) that allows the clamping arm 10 and the receiving arm 15 to rotate towards and away from each other in the C1 and C2 directions. The clamping arm has a T-like shape, and a needle deployment mechanism is disposed on a slightly-curved portion of the clamping arm 10 (cross-bar of the T). The needle deployment mechanism includes a guide rail 60, needle 40, a sliding component 55 that are curved to conform to the curved portion of the clamping arm 10. In other embodiments, the portion of the clamping arm 10 that holds the needle deployment mechanism, the guide rail 60, the needle 40 and the sliding component 55 are straight, curved, or a combination of both.

Figure 9:
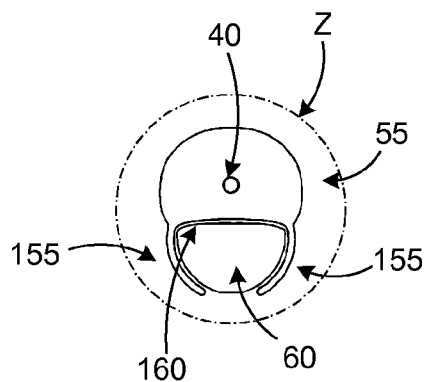
FIG. 9 is a cross-sectional view of a sliding component for certain embodiments of the multi-arm delivery device.

The guide rail 60 of multi-arm delivery device 200 is shown in greater detail in FIG. 9. FIG. 9 is the cross-sectional view of the Z-section from FIG. 8a. FIG. 9 shows a cross-sectional view of the sliding component 55 on the guide rail 60. In this embodiment, the sliding component 55 includes sliding members 155 that wrap at least partially around the guide rail 60 so that the sliding component 55 remains securely on the guide rail 60 during operation. The guide rail 60 has a top surface 160 along which the sliding component 55 can slidably move. The top surface 160 can be a curved surface and/or a flat surface. A portion of the needle is disposed within or coupled to the sliding component 55.

The distal end 35 of the receiving arm 15 is configured to releasably hold an implant 165, which is part of an implant assembly. The implant assembly includes the implant, i.e. sling, 165, and a capture portion 150 coupled to or formed as part of the implant 165. The capture portion 150 is also referred to the end portion of the implant 165.

The following describes the operational positions of the multi-arm delivery device 200 as shown in FIGS. 8a-8b.

FIG. 8a depicts the multi-arm delivery device 200 with the clamping arm 10 and receiving arm 15 in open configuration having the needle 40 in a retracted position. When the needle 40 is in this position, the distal end 45 of the needle 40 is stowed or held within the lumen 115 of the guide compartment 70.

FIG. 8b depicts the multi-arm delivery device 200 having the clamping arm 10 and receiving arm 15 in a partially clamped position. In operation, tissue and/or a ligament may be placed in the space S between the clamping 10 arm and receiving arm 15. The sliding component moved in the C1 direction so that the needle 40 is advanced across the space S and into the distal end 35 of the receiving arm 15 where the capture portion 55 of the implant is releasably held. Within Section Y, the needle 40 captures the end portion of the implant 55. The capture event that occurs in Section Y is shown in FIGS. 13c-13e, 14c-14e, 15c-15e and described in the corresponded text.

FIG. 8c depicts the needle 40 retracting out of the distal end 35 of the receiving arm 15 as the sliding component 55 is moved in the D2 direction. As shown, the needle 40 has the capture portion 55 of the implant 165 disposed within the retaining slot 215 of the needle 40. As the needle 40 retracts, the needle pulls at least a portion of the implant 165 along the path of the needle 40 across space S. The retraction of the needle with the captured implant allows the operator of the device 200 position the implant into the desired location. If the needle penetrated tissue, the retraction of the needle allows the operator to position the implant 165 substantially along the needle path through tissue. If the needle does not penetrate tissue, it allows the operator to position the sling around tissue, ligaments, etc. disposed within the space S between the receiving arm 15 and clamping arm 10. Both movement of the sliding component in the D2 direction and movement of the clamping arm in the C2 direction can cause the needle 40 to retract out of the distal portion 35 of the receiving arm 15.

In certain aspects, the multi-arm delivery device utilizes a needle 40 that includes a plurality of retaining slots 215 and pointed tip 120 at the distal end of the needle 40. In certain embodiments, the pointed tip 120 is a tissue penetrating tip. In some embodiments, pointed tip 120 may include multiple facets or edges. Each retaining slot 215 defines a recess within the body of the needle 40 and includes an angled inner wall designed to hook/retain at least some of the capture portion during retraction of the needle 40. The plurality of retaining slots 215 provides for a higher capture probability because the plurality of retaining slots 215 increases the surface area of the needle that is capable of retaining at least some of the capture portion 55. Any configuration of retaining slots 215 is suitable for use in the invention. For example, the retaining slots 215 can be placed in an organized fashion around the needle 40 or placed randomly on the needle 40. For example, needle 40 can have two retaining slots 215 disposed on the same cross-section, three retaining slots 215 disposed on the same cross section, two retaining slots 215 in a row on the top of the needle, two retaining slots 215 in a row on the bottom of the needle, etc.

Figure 12A:
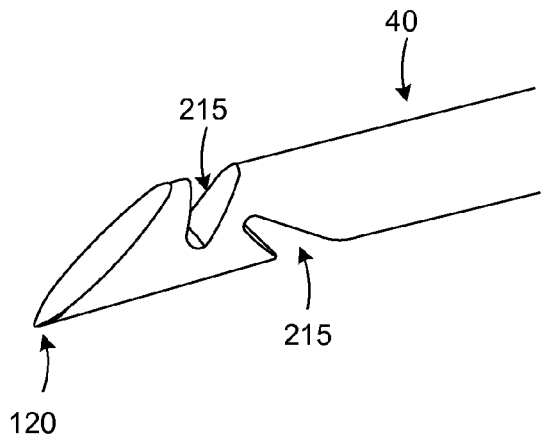
FIGS. 12a-12d depict various embodiments of a needle that includes a plurality of retaining slots.
Figure 12B:
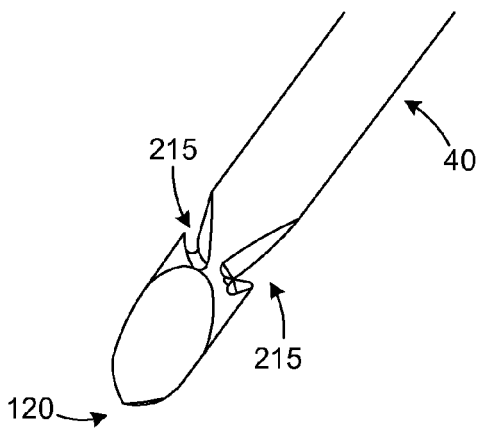
Figure 12C:
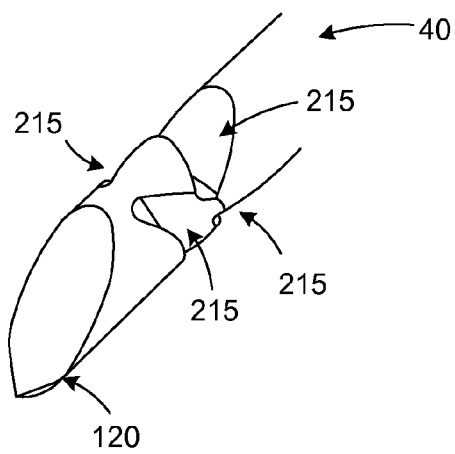
Figure 12D:
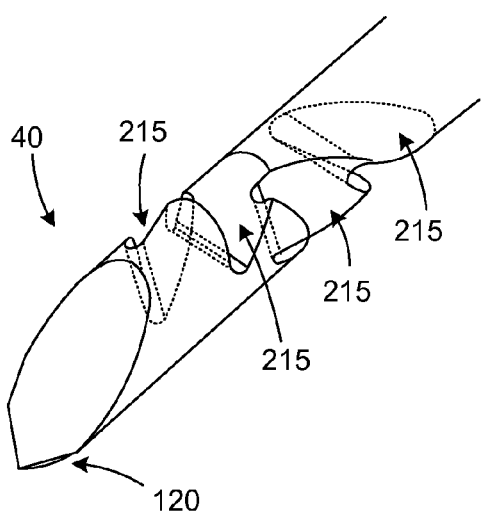

FIGS. 12a-12d exemplify various embodiments of a needle 40 with a plurality of retaining slots 215. FIG. 12a shows a needle 40 having a top retaining slot 215 and a bottom retaining slot 215. FIG. 12b shows a needle 40 having a first side retaining slot 215 and a second side retaining slot 215. FIG. 12c illustrates a needle 40 with four retaining slots 215, which includes a first set of two retaining slots near the needle tip 120 and a second set of two retaining slots proximal to the first set. The retaining slots 215 of each set are open in the opposite direction. As shown in FIG. 12c, one set of retaining slots 215 defines recesses that are open on the side of the needle body, and the other more proximal set of retaining slots 215 defines recesses that are open from the top and bottom of the needle body. FIG. 12d illustrates four retaining slots 215 in a spiral formation around the needle 40.

Figure 10:
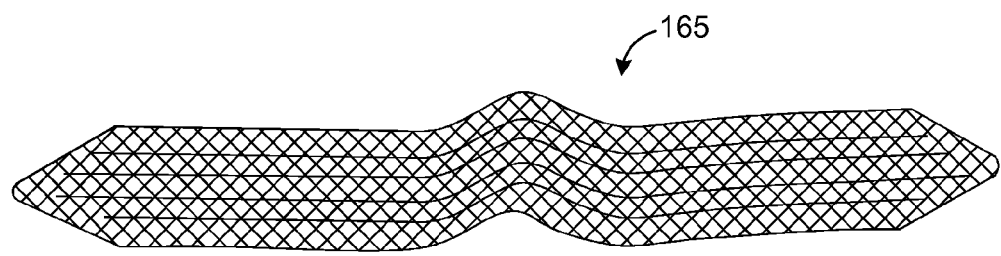
FIG. 10 depicts a sling for use with embodiments of the multi-arm delivery device.

The implants, or slings, 165 for use with the multi-arm delivery devices can include a wide variety of shapes and sizes, materials and treatments. While the sling 165 is preferably rectangular for treating incontinence, other shapes are also contemplated. Depending on the treatment addressed (e.g. to provide hammock support for the bladder or bladder neck, or to address a rectocele, enterocele or prolapse) the sling may be any of a wide variety of shapes. As an example, the sling may be of the general shape of the slings described and shown in Moir et al., The Gauze-Hammock Operation, Journal of Obstetrics and Gynaecology of the British Commonwealth, Volume 75, No. 1, Pps. 1-9 (1968). FIG. 10 illustrates a rectangular sling 65 suitable for use in the invention.

Figure 11:
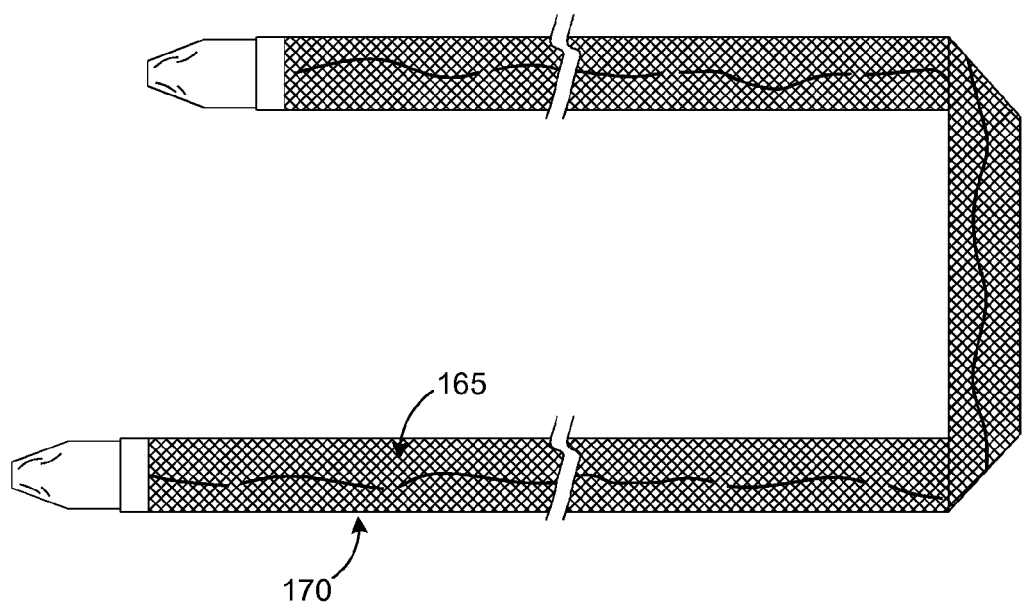
FIG. 11 depicts a sling disposed within a protective sheath for use with embodiments of the multi-arm delivery device.

The sling 165 can also be formed in a protective sheath 170 which surrounds the sling 165, as shown in FIG. 11. The protective sheath 170 is used to facilitate delivery of the sling 165 without friction against the body tissue, ligaments, organs, etc. Once the sling 165 is placed into the desired position, the protective sheath 170 is typically removed. In some embodiments, the sheath 170 extends along substantially the full length of the implant. In some embodiments, the sheath may extend along only a portion of the length of the implant. In some embodiments, more than one sheath is utilized. As an alternative to the protective sheath, any other packaging can be used, such as a sleeve.

In certain embodiments, sheath 170 and the implant 165 are made of materials having sufficient strength and structural integrity to withstand the various forces exerted upon these components during an implant delivery procedure and/or following implantation within a patient.

In one embodiment, the sling 165 is made of a mesh material. The mesh material comprises one or more woven or inter-linked filaments or fibers that form multiple fiber junctions throughout the mesh. The fiber junctions may be formed via weaving, bonding, ultrasonic welding or other junction forming techniques, including combinations thereof. In addition, the size of the resultant openings or pores of the mesh should be sufficient to allow tissue in-growth and fixation within surrounding tissue. As an example, not intended to be limiting, the holes may comprise polygonal shaped holes with diagonals of 0.132 inches and 0.076 inches. The quantity and type of fiber junctions, fiber weave, pattern, and material type influence various sling properties or characteristics. In some embodiments, the mesh material comprises the least amount of material necessary to perform its function. Less material may promote quicker ingrowth of tissue through the mesh and may promote better securement at the implantation site.

There are many suitable mesh materials, and the implant may, in the alternative or in combination, be made of non-mesh materials. Exemplary mesh materials include, for example, synthetic materials, natural materials (e.g., biological) or a combination thereof. The mesh may be fabricated from any of a number of biocompatible materials, such as nylon, silicone, polyethylene, polyester, polyethylene, polyimide, polyurethane, polypropylene, fluoropolymers, copolymers thereof, combinations thereof, or other suitable synthetic material(s). The material may be, for example, a biodegradable synthetic material. The term "biodegradable," as used herein, refers to the property of a material that dissolves in the body. Such materials may also be absorbed into the body, i.e., bioabsorbable.

The sheath 170 can be fabricated from, without limitation, polyethylene, polypropylene, nylon, polyester or Teflon.

In some aspects, the ends of the implant 165 or the ends of the protective sheath 170 having an implant 165 disposed therein are attached to capture portions 55 to form an implant assembly. Typically, the capture portions 55 are attached to the implant 165 or to the protective sheath 170 via a suture or other connecting element. It is also contemplated that the implant 165 or sheath 170 may have any number of ends, and the capture portion may be coupled to one end, a few of the ends, or all of the ends. In another embodiment, the implant 165 and protective sheath 170 are not coupled to the capture portion 55, but rather the capture portion 55 is formed as part of the implant 165 or sheath 170 (i.e. the capture portion is the actual end portion of the implant or sheath).

Figure 13A:
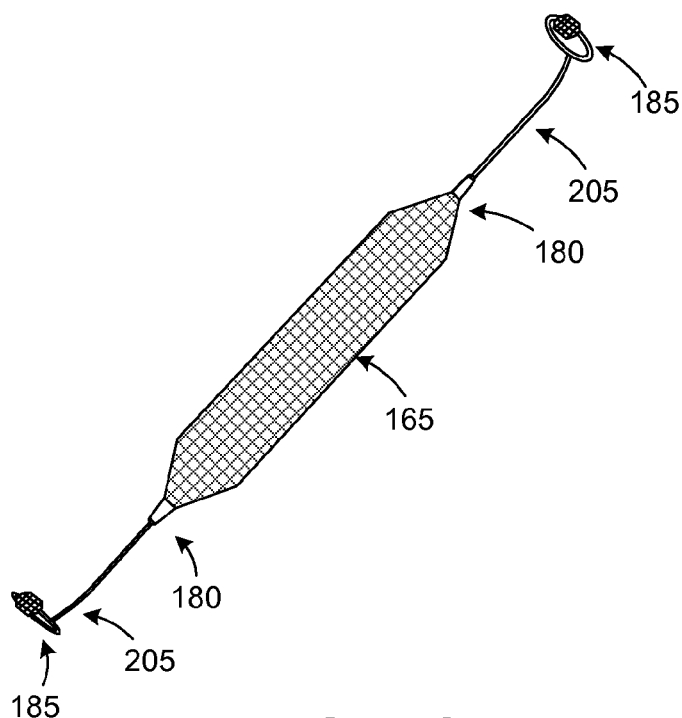
FIG. 13a depicts an implant assembly with a mesh catch.
Figure 14A:
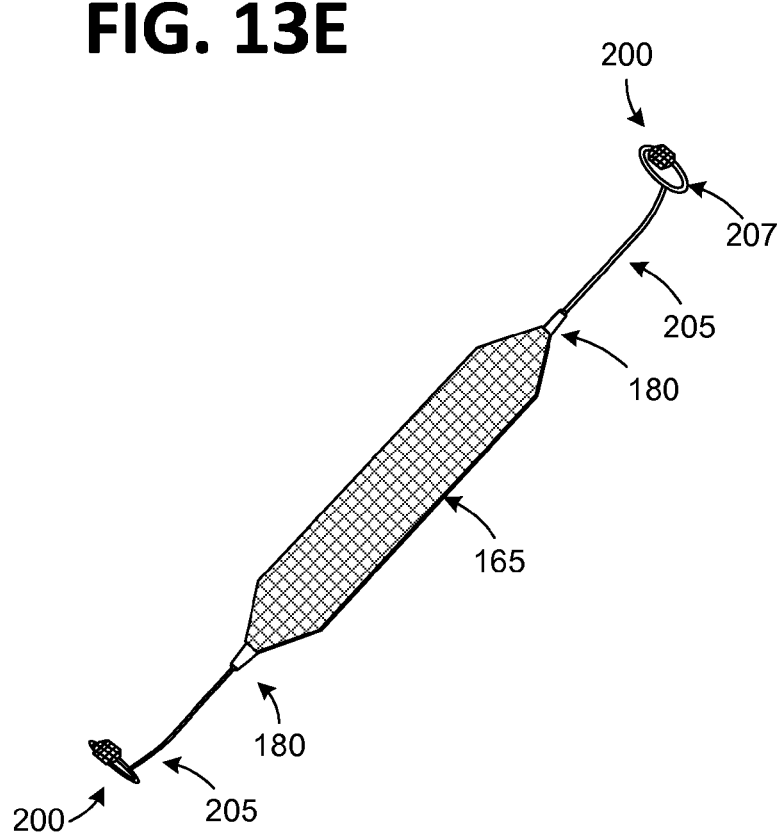
FIG. 14a depicts an implant assembly with an embodiment of a bundled catch.
Figure 14B:
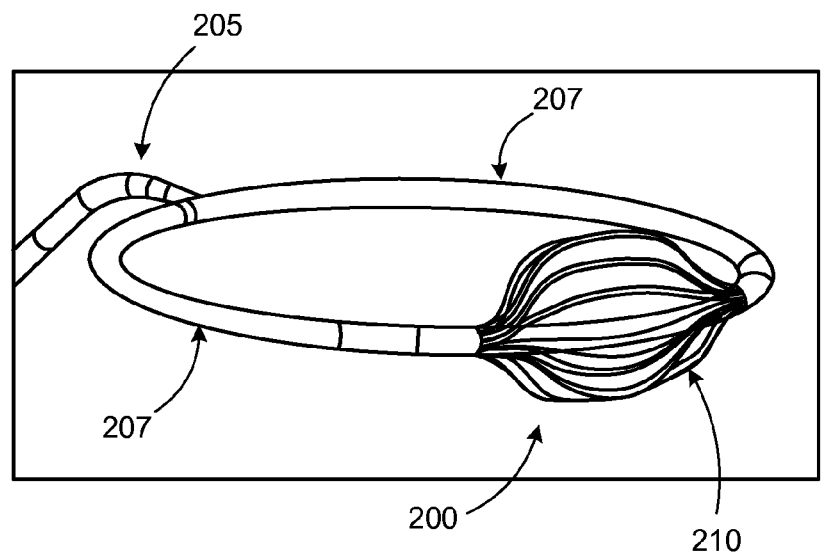
Figure 15A:
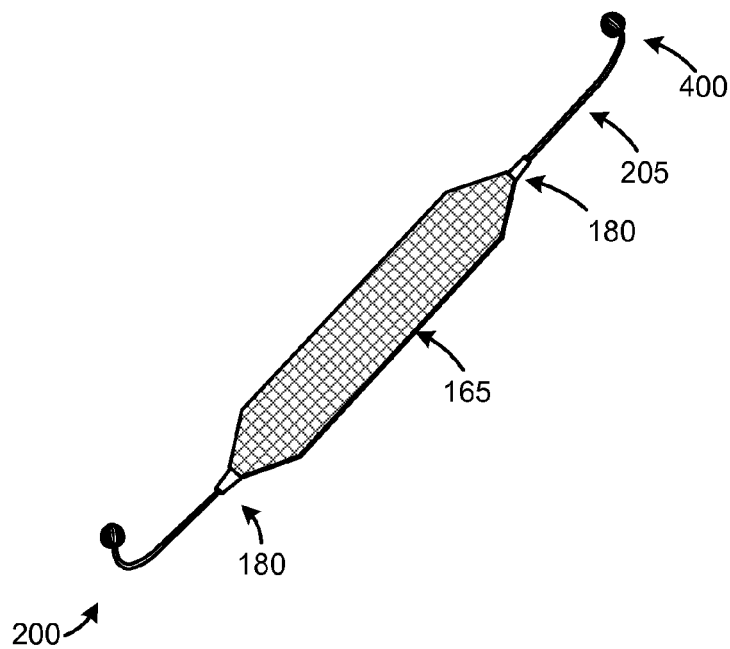
FIG. 15a depicts an implant assembly with another embodiment of a bundled catch.

Various embodiments of implant assemblies are shown FIGS. 13a, 14a, and 15a. As shown in FIGS. 13a, 14a, and 15a, each implant assembly includes an implant or sling 165 that are coupled to attachment members 180. A suture 205, or other cord-like member, is coupled to the attachment member 180 and extends to a capture portion 55 (shown as 185 in FIG. 13a, 200 in FIG. 14a, and 400 in 15a). The suture 205 may be coupled to the capture portion in any suitable manner to allow the capture portion to be releasably-held within receiving arm 15. As best shown in FIG. 14b, the suture 205 can be split into two separate arms 207 then coupled to the sides of the capture portion 200. Alternatively, the suture 205 can be directly attached to the capture portion 400, as shown in FIGS. 15a-15d.

In certain aspects, the capture portion 55, as used with the multi-arm delivery devices of the invention, is disposed within the distal end 35 of the receiving arm 15 so that the needle 40 advances substantially perpendicular to the body of the capture portion 55. In other words, the capture portion defines a plane that is substantially perpendicular to the advancing needle 40. As the needle 40 advances, at least a portion of the needle 40 enters substantially perpendicular into the capture portion 55, and, as the needle 40 retracts, the needle 40 retains at least some of the capture portion 55 into at least one of the needle's 40 retaining slots 215. A portion of the needle 40 may partially enter the capture portion 55 or a portion of the needle 40 may pass through the capture portion 55 prior to retraction.

Figure 13B:
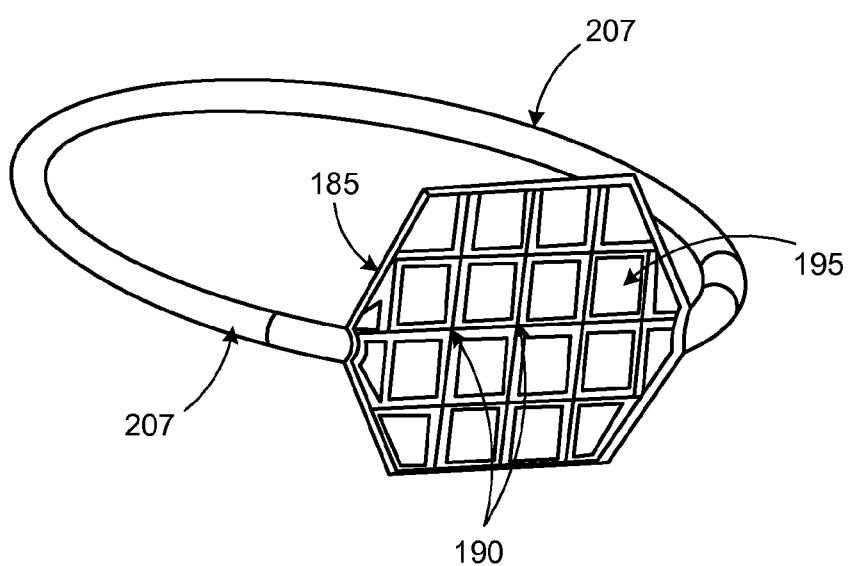
Figure 13C:
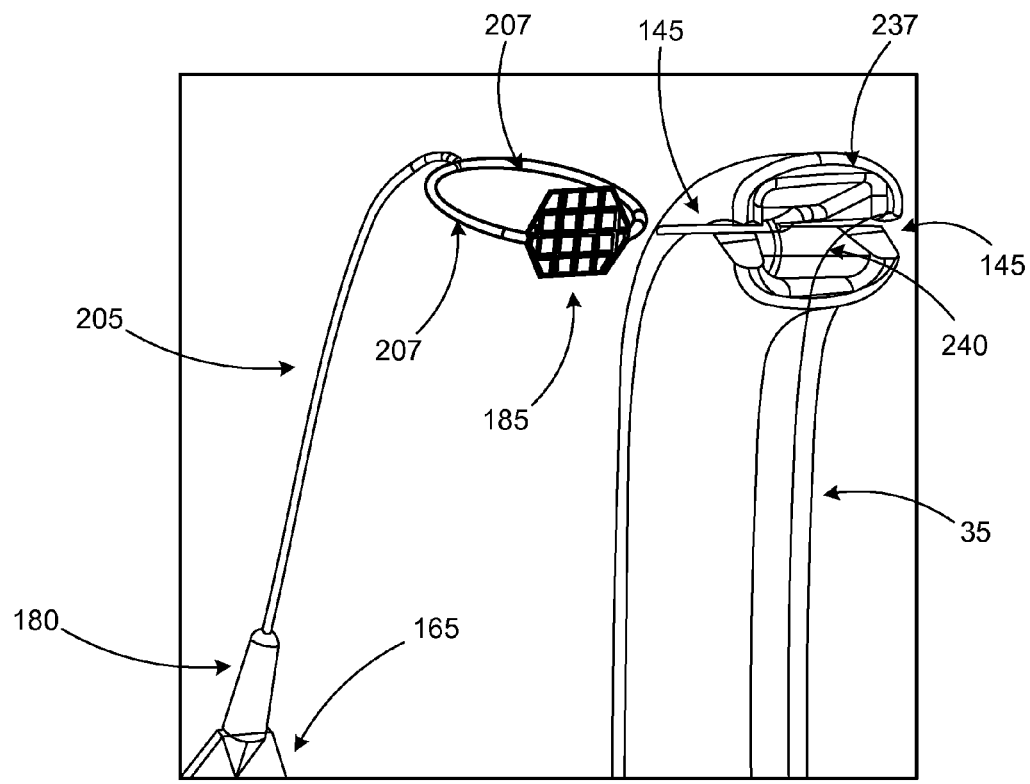
FIGS. 13c-13e illustrate the implant assembly of FIG. 13a in use with the multi-arm delivery device.
Figure 13D:
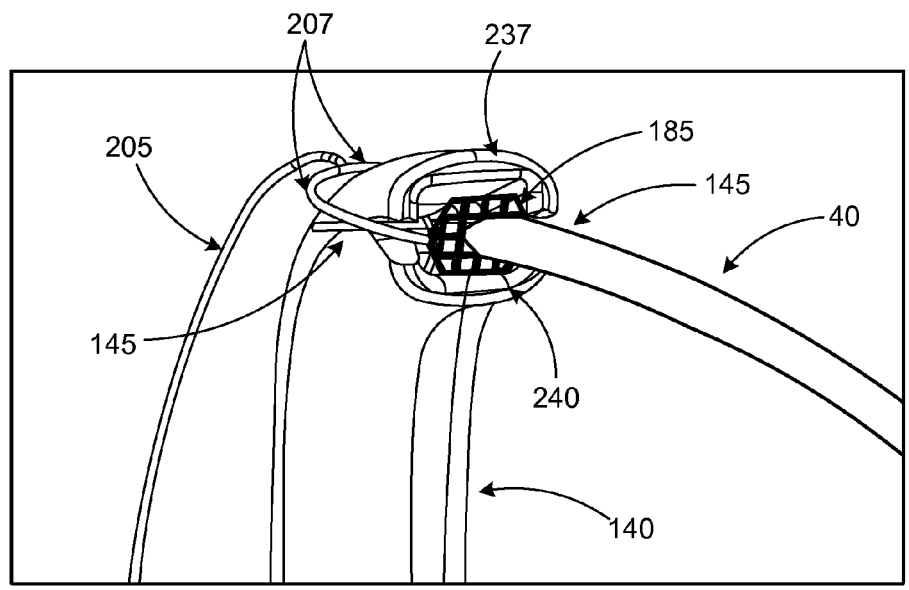
Figure 13E:
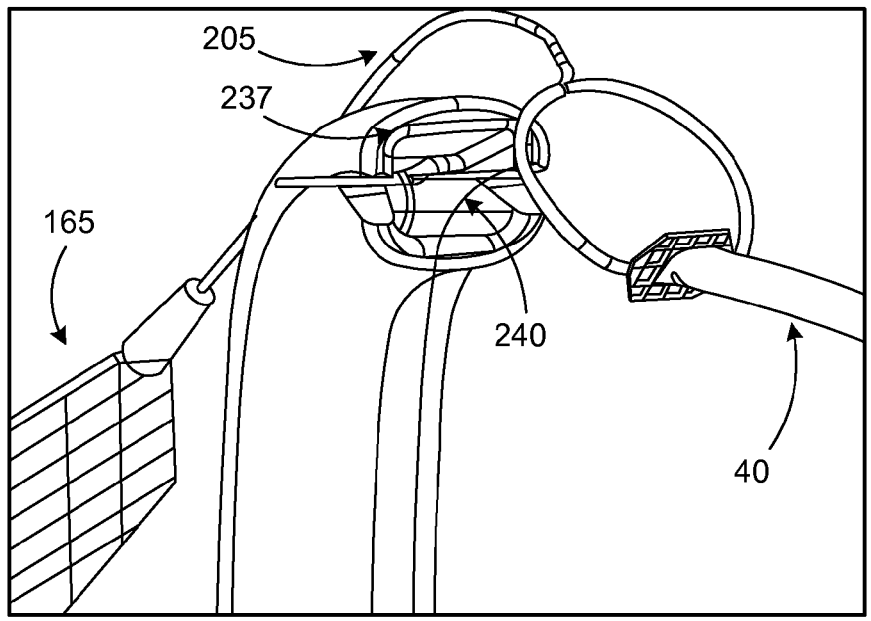

As shown FIGS. 13a-13f, the capture portion 55 is a mesh catch 185. FIG. 13b shows a close-up of mesh catch 185. The mesh catch 185 has a plurality of openings 195. Because the needle 40 can enter any one of the plurality of openings to capture the implant, the mesh catch greatly increasing the acceptance range of the needle 40 and the probability that the needle 40 will capture the implant assembly to position the sling 165. Each opening is defined by at least one flexible edge, or wall, 195 of the mesh catch 185. The mesh catch can be formed from a single structure, e.g. a synthetic mesh formed in a mold, or, alternatively, the mesh catch is a net, e.g. mesh formed by knotting together, for example, twine, cords, rope, or thread. The mesh catch 185 can be directly attached to a suture 205 or attached to two or more arms 207 extending from the suture 205. FIG. 13d shows the mesh catch coupled to the implant 165 prior to placement of the mesh catch 185 into the cavity 240 of the distal end 35 of the receiving arm 15. FIG. 13e depicts the mesh catch 185 disposed within the cavity 240. The arms 207 coupled to the mesh catch 185 are releasably held within the slits 145. The mesh catch 185, as disposed within the cavity 240, is substantially perpendicular to the advanced needle 40. As further shown in FIG. 13e, the distal portion of the needle 40 enters into one of the plurality of openings 195. As the needle 40 advances into one of the plurality of openings 195, the flexible edge 190 of the opening moves to allow the needle 40 to pass through the opening 195. When a retaining slot 215 of the needle 40 passes the flexible edge 190, the flexible edge 190 moves into the retaining slot 215. This movement of the flexible edge 190 into the retaining slot 215 allows the needle 40 to capture the implant assembly.

FIG. 13f shows a partially retracted needle 40 with the mesh catch 185 retained/captured within one of the needle's 40 retaining slots 215. As the needle 40 retracts, the needle 40 pulls the mesh catch 185 along with the sling 165 and delivers the sling 165 to a desired position.

In other embodiments, the capture portion 55 is a bundled catch. The bundle catch is a three-dimensional catch defining a volume that is configured to receive at least a portion of the needle into the bundle catch. In addition, at least a portion of the bundled catch is configured to enter one or more retaining slots of the needle 40. Various embodiments of the bundled catch are described hereinafter.

As shown in FIG. 14b, the bundled catch 200 comprises a plurality of flexible curved members 210 disposed between two arms 207 to form a sphere-like shape. The flexible curved members 210 flex to allow the needle 40 to enter into the body of the bundled catch 200. When a retaining slot 215 of the needle 40 passes by one of the flexible curved members 210, the flexible curved member 210 can enter one or more retaining slots 215. This allows the retaining slot 215 to capture the implant assembly. One or more of the plurality of flexible curved members 210 can enter any one of a plurality of retaining slots 215 disposed on a needle 40.

Figure 14C:
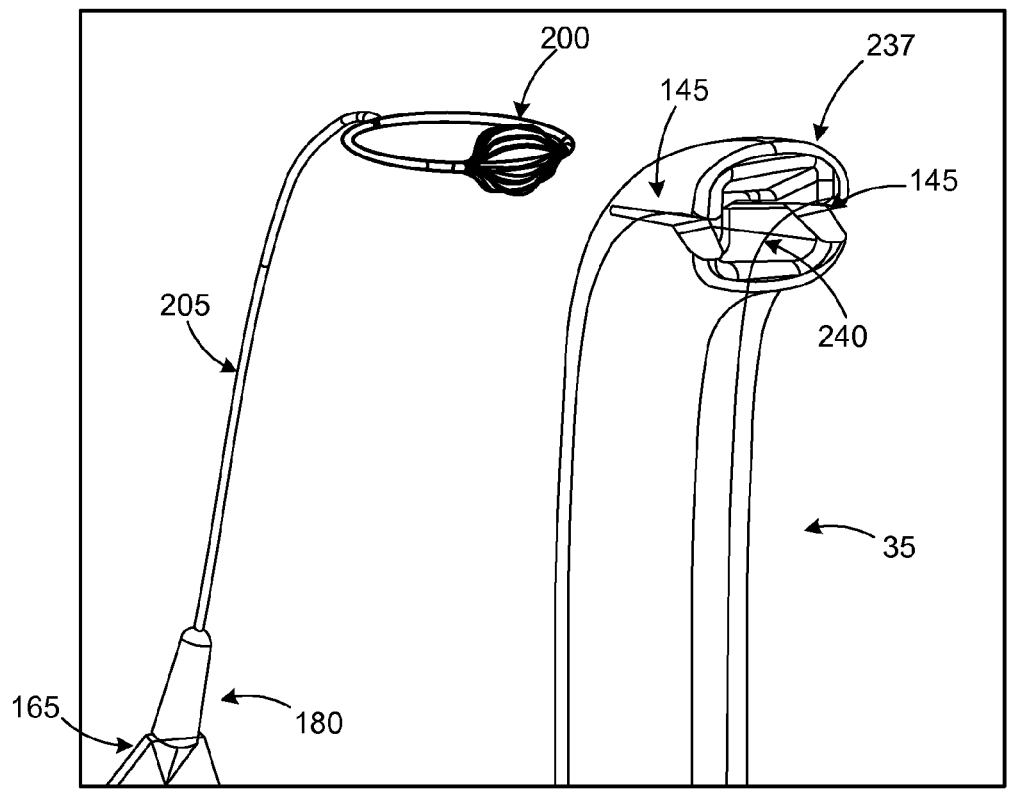
FIGS. 14c-14e illustrate the implant assembly of FIG. 14a in use with the multi-arm delivery device.
Figure 14D:
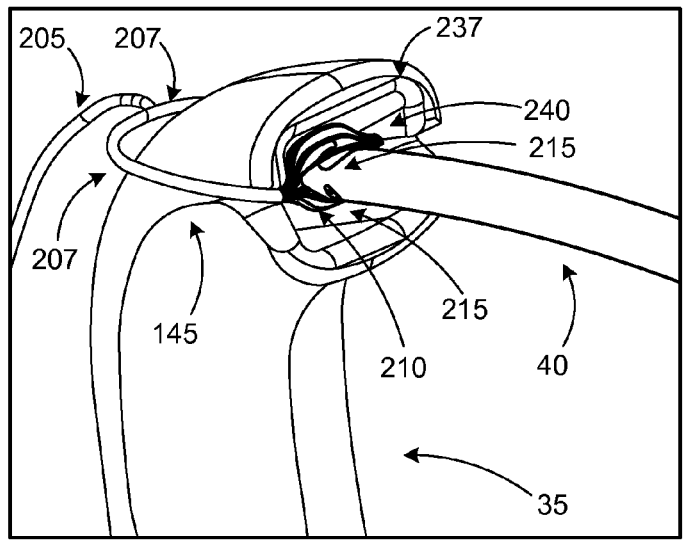
Figure 14E:
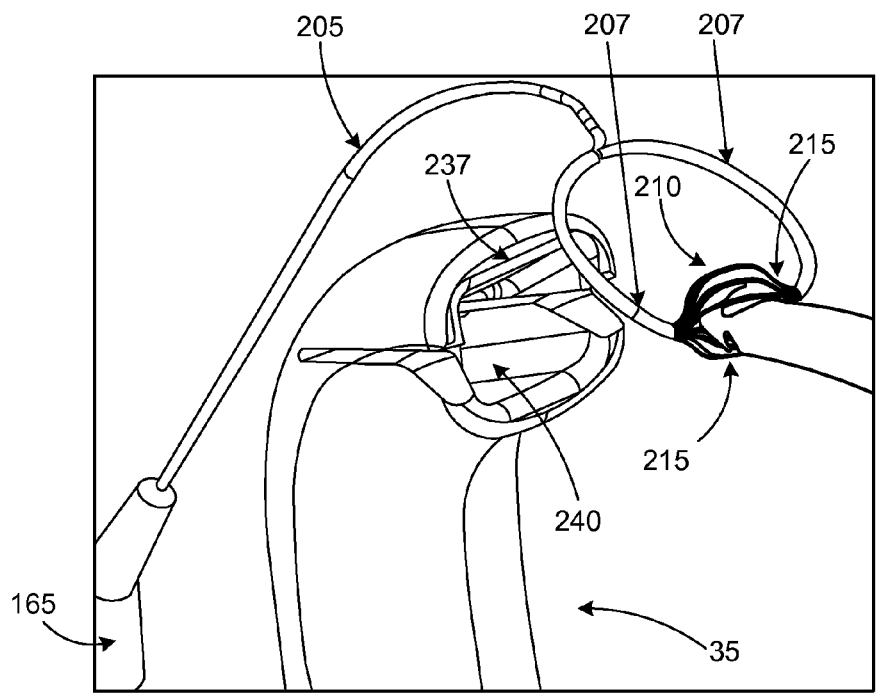

FIG. 14c depicts the bundled catch 200 prior to placement within the cavity 240 of the distal end 35 of the receiving arm 15. As shown in FIG. 14d, the arms 207 are disposed within the slits 145 to releasably hold the bundled catch within the cavity 240 of the distal end 35 of the receiving arm 15. FIG. 14d also shows the distal end 45 of the advanced needle 40 as received into the body of the bundled catch 200, and shows the flexible curved members 210 as entered into the retaining slots 215 of the needle 40. The needle 40 has retaining slots 215 located on the top portion and bottom portion that align with the direction of the flexible curved members 210 for capture. FIG. 14e shows the needle 40 partially retracted with the bundled catch 200 captured in the retaining slots 215. As the needle 40 continues to retract, the needle 40 pulls the bundle catch 200 along with the sling 165 and delivers the sling 165 to a desired position.

Figure 15B:
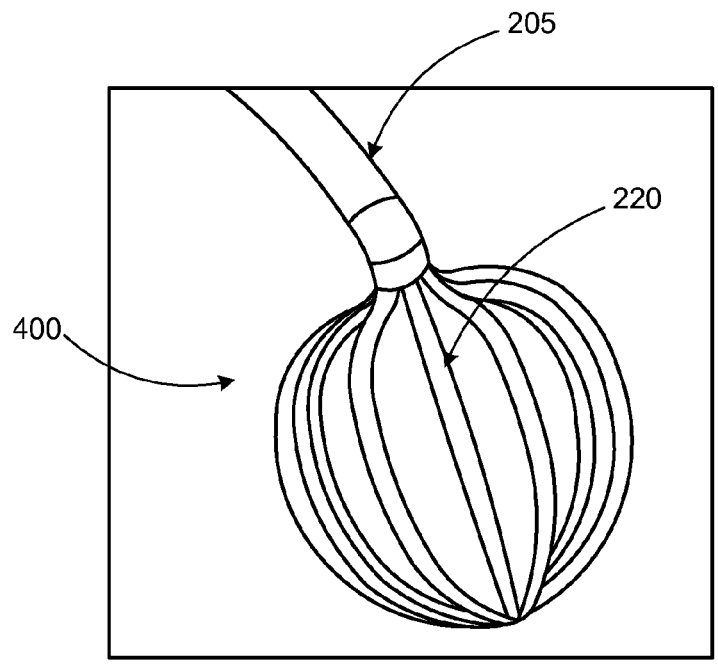
Figure 15C:
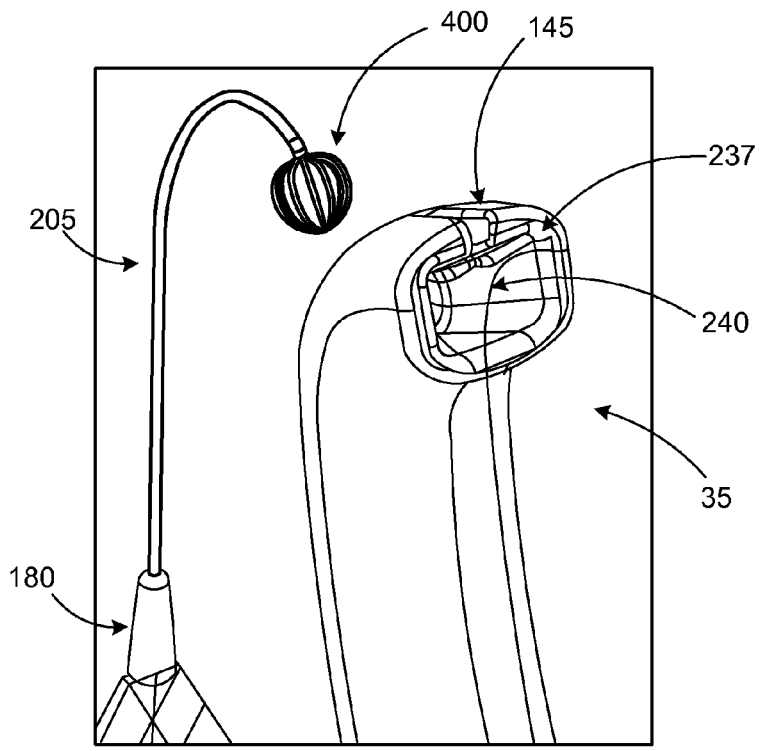
FIGS. 15c-15e illustrate the implant assembly of FIG. 15a in use with the multi-arm delivery device.
Figure 15D:
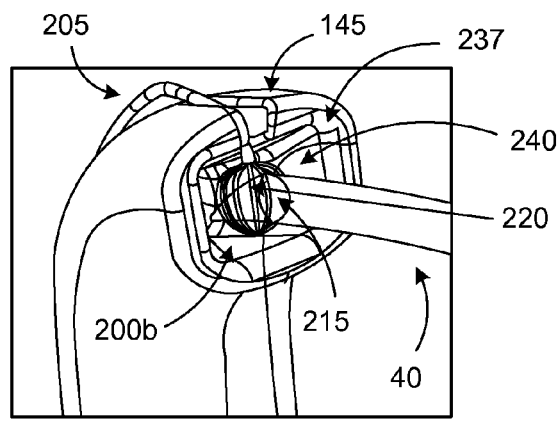
Figure 15E:
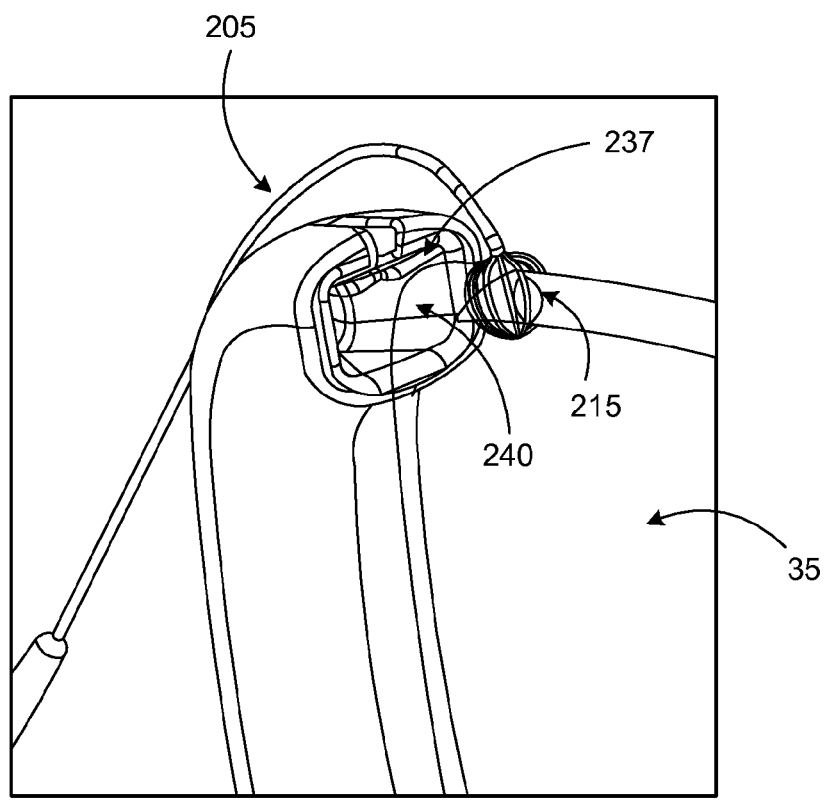

As shown in FIG. 15b, the three-dimensional bundle catch 400 that includes a plurality of looped members 220 connected directly connected to the suture 205. In one embodiment, the looped members 220 are flexible with some rigidity. FIG. 15b shows close-up view of the bundle catch 400 with a plurality of semi-rigid looped members 220 that form a spherically-shaped catch, which resembles the looped wires that form a whisk. Alternatively, the looped members 220 can include a plurality of looped non-rigid members, e.g. series of looped cords or threads.

FIG. 15c shows the bundled catch 400 prior to placement within the cavity 240 of the distal end 35 of the receiving arm 15. Because the bundle catch 400 is attached directly to the suture 205, the distal end 35 of the receiving arm has one slit 145 for releasably holding the bundle catch 400. FIG. 14d shows the bundle catch 400 disposed within the cavity 240 of the distal end 35. As disposed within the catch, the looped members 240 are in a vertical orientation. The needle 40 is shown advanced into bundle catch 40. The needle 40 has retaining slots 215 on the sides of the needle 40 to allow the vertically orientated looped members 240 to enter the retaining slots 215. FIG. 14e shows the needle 40 partially retracted with the bundled catch 400 captured in at least one of the retaining slots 215. As the needle 40 continues to retract, the needle 40 pulls the bundle catch 400 along with the sling 165 and delivers the sling 165 to a desired position.

Figure 16:
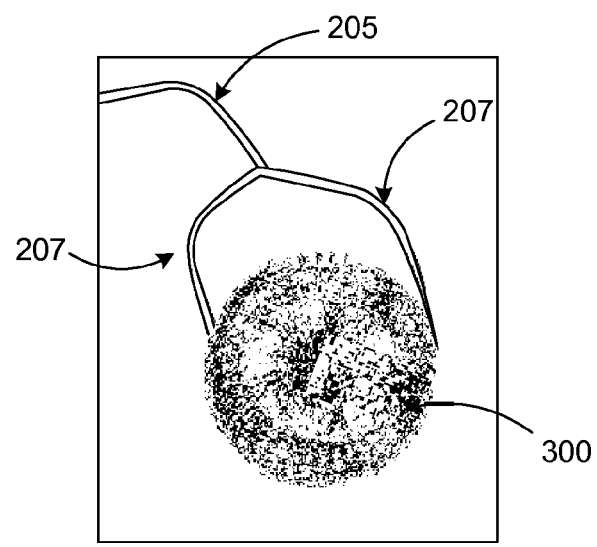
FIG. 16 depicts a close up view of yet another embodiment of a bundled catch.

FIG. 16 shows a three-dimensional bundle catch 300 that is a threaded/netted ball structure. Although not shown, the bundle catch 300 can be part of an implant assembly like other embodiments of the bundle catch 200 and 400. The bundle catch 300 has multiple layers of threaded/netted material arranged in a ball-like structure. The layers of netted/threaded material are preferably loosely-packed to allow the distal end 45 of a needle 40 to enter and/or pass through the bundle catch 300. As the needle 40 retracts, at least a portion of the bundle catch 300 is deposited in one or more retaining slots 215 of the needle 40. This allows the needle to pull the bundle catch 300 along with the sling 165 and deliver the sling to a desired position.

The capture portions described above can be formed from many suitable materials. Exemplary materials include, for example, synthetic materials, natural materials or a combination thereof. The capture portion may be formed in any manner including but not limited to knitting, weaving, non-woven constructions, braiding, layered filaments or materials. The capture portion may be fabricated from any of a number of biocompatible materials, such as nylon, silicone, polyethylene, polyester, polyethylene, polyimide, polyurethane, polypropylene, fluoropolymers, copolymers thereof, combinations thereof, or other suitable synthetic material(s). In some embodiments, the capture portions comprise a sheet or layer of material that can be pierced by a needle for capture.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A medical device for delivering an implant into the body of a patient, comprising:
   a first portion comprising a handle, a junction section extending distally from the handle, and a needle-receiving arm extending distally from the junction section, at least a portion of the needle-receiving arm being curved, the needle-receiving arm comprising a distal portion configured to releasably hold an end portion of the implant, the distal portion defining an opening leading to a cavity;
   a needle having a plurality of retaining slots; and
   a second portion comprising a clamping arm movably coupled to the junction section to allow an operator of the medical device to hold the handle and manually move the clamping arm with respect to the first portion, at least a portion of the clamping arm being curved,
   the clamping arm comprising a needle deployment mechanism having a sliding component operatively coupled to the needle, the needle deployment mechanism for advancing the needle through tissue of the body of the patient into the cavity of the distal portion of the needle-receiving arm to allow at least some of the releasably-held implant end portion to be disposed in at least one of the plurality of retaining slots of the needle, and the needle deployment mechanism also for retracting the advanced needle out of the cavity and back through the tissue to pull the end portion of the implant through the tissue.

2. The medical device of claim 1 wherein two or more of the plurality of retaining slots are spirally-aligned on the needle.

3. The medical device of claim 1 wherein the needle also comprises a tissue-penetrating tip, and one or more of the plurality of retaining slots are disposed distal to one or more others of the plurality of retaining slots.

4. The medical device of claim 1 wherein the implant end portion comprises a mesh catch comprising a plurality of openings for receiving the advanced needle.

5. The medical device of claim 4 wherein each of the plurality of openings of the mesh catch is defined by at least one flexible edge configured to move.

6. The medical device of claim 5 wherein at team, one of the flexible edges moves as the needle advances into one of the plurality of openings of the mesh catch, and this at least one of the flexible edge moves into at least one retaining slot as the needle is retracted.

7. The medical device of claim 5 Wherein the mesh catch is coupled to at least one suture.

8. The medical device of claim 1 wherein the implant end portion comprises a bundled catch defining a volume.

9. The medical device of claim 8 wherein at least a portion of the advancing needle enters into the bundled catch, and a portion of the bundled catch is configured to enter one or more of the plurality of retaining slots as the advanced needle retracts.

10. The medical device of claim 8 wherein the bundled catch comprises a plurality of flexible members spherically disposed between two suture arms for receiving the needle.

11. The medical device of claim 8 wherein the bundled catch comprises a plurality of looped members for receiving the needle.

12. The medical device of claim 8 wherein the bundled catch is coupled to at least one suture arm.

13. The medical device of claim 8, wherein the bundled catch comprises a netted or threaded ball.

14. The medical device of claim 1 wherein the implant is a sling configured for implantation into the body of the patient to treat female urinary incontinence by raising or supporting the patient's bladder neck or urethra.

15. The medical device of claim 1 wherein the distal portion of the needle-receiving arm further comprises at least one slit for releaseably holding the implant end portion in the cavity.

16. The medical device of claim 1 wherein the needle deployment mechanism of the clamping arm has a distal portion and a proximal portion and comprises the sliding component and a curved guide rail, the sliding component movably coupled to the curved guide rail to allow the operator to move the sliding component distally along the curved guide rail to advance the needle and to move the sliding component proximally along the curved guide rail to retract the needle.

* * * * *